United States Patent
Kadyrov

(10) Patent No.: US 9,878,975 B2
(45) Date of Patent: Jan. 30, 2018

(54) CATALYTIC HYDROGENATION FOR PRODUCING AMINES FROM CARBOXYLIC ACID AMIDES, CARBOXYLIC ACID DIAMIDES, DI-, TRI-, OR POLYPEPTIDES, OR PEPTIDE AMIDES

(71) Applicant: Evonik Degussa GmbH, Essen (DE)

(72) Inventor: Renat Kadyrov, Frankfurt (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/034,120

(22) PCT Filed: Oct. 16, 2014

(86) PCT No.: PCT/EP2014/072184
§ 371 (c)(1),
(2) Date: May 3, 2016

(87) PCT Pub. No.: WO2015/067450
PCT Pub. Date: May 14, 2015

(65) Prior Publication Data
US 2016/0272571 A1   Sep. 22, 2016

(30) Foreign Application Priority Data
Nov. 5, 2013   (EP) ..................................... 13191503

(51) Int. Cl.
| | | |
|---|---|---|
| C07C 209/50 | (2006.01) |
| C07B 43/04 | (2006.01) |
| C07C 227/16 | (2006.01) |
| C07D 265/32 | (2006.01) |
| C07D 207/16 | (2006.01) |
| C07K 5/062 | (2006.01) |
| C07D 295/03 | (2006.01) |
| C07D 295/15 | (2006.01) |
| C07F 9/40 | (2006.01) |
| C07K 5/065 | (2006.01) |
| C07D 295/027 | (2006.01) |

(52) U.S. Cl.
CPC ............ *C07C 209/50* (2013.01); *C07B 43/04* (2013.01); *C07C 227/16* (2013.01); *C07D 207/16* (2013.01); *C07D 265/32* (2013.01); *C07D 295/027* (2013.01); *C07D 295/03* (2013.01); *C07D 295/15* (2013.01); *C07F 9/4006* (2013.01); *C07F 9/4062* (2013.01); *C07K 5/06026* (2013.01); *C07K 5/06078* (2013.01)

(58) Field of Classification Search
None
See application file for complete search history.

(56) References Cited

U.S. PATENT DOCUMENTS

| | | |
|---|---|---|
| 4,141,917 A | 2/1979 | Kunstmann et al. |
| 2012/0253042 A1 | 10/2012 | Milstein et al. |
| 2016/0264513 A1 | 9/2016 | Kadyrov |

FOREIGN PATENT DOCUMENTS

DE   604 277   10/1934

OTHER PUBLICATIONS

English translation of portion of Office Action for counterpart Chinese application 201480072289.6 filed Oct. 16, 2014.
Xiao, et al., "A Direct and General Method for the Reductive Alkylation of Tertiary Lactams/Amides: Application to the Step Economical Synthesis of Alkaloid (-)-Morusimic Acid D," *J. Org. Chem.* 78:8305-8311 (Aug. 2013).
English translation of the International Search Report for PCT/EP2014/072184 filed Oct. 16, 2014.
English translation of the Written Opinion of the International Searching Authority for PCT/EP2014/072184 filed Oct. 16, 2014.
English translation of the International Preliminary Report on Patentability for PCT/EP2014/072184 filed Oct. 16, 2014.
European Search Report with partial machine translation attached for EP 13 19 1503 (related to PCT/EP2014/072184) dated Mar. 13, 2014.
English translation of the International Search Report for PCT/EP2014/072109 (international stage of copending U.S. Appl. No. 15/034,135) filed Oct. 15, 2014.
English translation of the Written Opinion of the International Searching Authority for PCT/EP2014/072109 filed Oct. 15, 2014.
English translation of the International Preliminary Report on Patentability for PCT/EP2014/072109 filed Oct. 15, 2014.
European Search Report with partial machine translation attached for EP 13 19 1498 (related to PCT/EP2014/072109) dated Mar. 13, 2014.
Balaraman, et al., "Direct Hydrogenation of Amides to Alcohols and Amines under Mild Conditions," *J. Am. Chem. Soc.* 132(47):16756-16758 (Dec. 2010).
Sashida, et al., "Studies on Diazepines. XXIX.[1)] Syntheses of 3H- and 5H-1,4-Benzodiazepines from 3-Azidoquinolines," *Chemical and Pharmaceutical Bulletin, Pharmaceutical Society of Japan* vol. 35:4110-4116 (Jan. 1987).

(Continued)

*Primary Examiner* — Clinton Brooks
(74) *Attorney, Agent, or Firm* — Law Office of: Michael A. Sanzo, LLC

(57) ABSTRACT

The present invention relates to a process for the preparation of amines, comprising the following steps: a. reaction of a (i) carboxylic acid amide of the general formula (I), or (ii) carboxylic acid diamide of the general formula (II), or (iii) di-, tri- or polypeptide, or (iv) peptide amide with carboxy-terminal amide function with an alkylating agent, b. addition of a hydrogenation catalyst to the reaction mixture in a molar ratio of from 1:10 to 1:100 000, based on carboxylic acid amide, carboxylic acid diamide, di-, tri- or polypeptide or peptide amide, c. reaction of the reaction mixture with hydrogen, where a hydrogen pressure of from 0.1 bar to 200 bar is established and where a temperature in a range of from 0° C. to 250° C. is established.

20 Claims, No Drawings

(56) References Cited

OTHER PUBLICATIONS

Stein, et al., "Catalytic Hydrogenation of Amides to Amines under Mild Conditions," *Angew. Chem. Int.* 52(8):2231-2234 (Feb. 2013).
Nishimura, "Handbook of Heterogeneous Catalytic Hydrogenation for Organic Synthesis," pp. 406-411, John Wiley and Sons, Inc., N.Y. (2001).
U.S. Appl. No. 15/034,135, filed May 3, 2016, Kadyrov.
Office Action for copending U.S. Appl. No. 15/034,135 dated Mar. 22, 2017.
Response to Office Action for copending U.S. Appl. No. 15/034,135 filed by Applicant on Jun. 21, 2017.

CATALYTIC HYDROGENATION FOR PRODUCING AMINES FROM CARBOXYLIC ACID AMIDES, CARBOXYLIC ACID DIAMIDES, DI-, TRI-, OR POLYPEPTIDES, OR PEPTIDE AMIDES

CROSS REFERENCE TO RELATED APPLICATIONS

The present application is US national stage of international application PCT/EP2014/072184, which had an international filing date of Oct. 16, 2014, and which was published in German on May 14, 2015. Priority is claimed to European application EP 13191503.5, filed on Nov. 5, 2013. The contents of the priority application is hereby incorporated by reference in its entirety.

The present invention relates to a process for the preparation of amines, comprising the following steps: a. reaction of a (i) carboxylic acid amide of the general formula (I), or (ii) carboxylic acid diamide of the general formula (II), or (iii) di-, tri- or polypeptide, or (iv) peptide amide with carboxy-terminal amide function with an alkylating agent, b. addition of a hydrogenation catalyst to the reaction mixture in a molar ratio of 1:10 to 1:100 000, based on carboxylic acid amide, carboxylic acid diamide, di-, tri- or polypeptide or peptide amide, c. reaction of the reaction mixture with hydrogen, where a hydrogen pressure of from 0.1 bar to 200 bar is established and where a temperature in a range of from 0° C. to 250° C. is established.

Reduction of carboxylic acid amides is one of the most important methods for the preparation of amines. The classic process is based on the reduction by complex hydrides, although stoichiometric amounts of hydride are required and the selectivity is relatively low. The development of catalytic reduction with hydrogen remains to date one of the greatest challenges. Hydrogenations of this kind are known in the literature, although large amounts (15 mol % and more) of catalyst, very high pressures and temperatures above 200° C. are necessary in order to achieve useable yields (S. Nishimura, Handbook of Heterogeneous Catalytic Hydrogenation for Organic Synthesis 2001, pp. 406-411, Wiley, N.Y.). The hydrogenation of tertiary and secondary carboxylic acid amides to give amines at 120-160° C. over a bimetallic Pd—Re catalyst has recently been reported (M. Stein, B. Breit, Angew. Chem. 2013, 125, 2287-2290). Despite somewhat milder conditions, however, a functional group is barely tolerated, even olefinic double bonds and aromatic rings are fully hydrogenated.

It is therefore the object of the present invention to provide an improved process for the catalytic hydrogenation of carboxylic acid amides by means of hydrogen which does not have the disadvantages of the direct hydrogenation used hitherto. Rather, attention should be directed to the mildness of the reaction conditions and large tolerance towards a very wide variety of functional groups.

Surprisingly, it has now been found that O-alkylated carboxylic acid amides can be hydrogenated to amines under very mild conditions in the presence of customary hydrogenation catalysts. The carboxylic acid amides can be O-alkylated here under very mild conditions easily and selectively "in situ" with an alkylating agent, consequently acid amides can ultimately be selectively hydrogenated to amines. Here, a very wide variety of functional groups are tolerated; inter alia, nitriles, carboxyl and phosphone groups are retained.

The technical object is achieved by a process for the preparation of amines comprising the following steps:

a) reaction of a
i. carboxylic acid amide of the general formula (I)

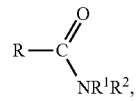

where
R is selected from the group consisting of H, $(C_1-C_{24})$-alkyl, $(C_3-C_{20})$-cycloalkyl, $(C_2-C_{13})$-heterocycloalkyl, $(C_6-C_{14})$-aryl, $(C_3-C_{13})$-heteroaryl and the acid radical of an amino acid selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine; and
$R^1$ and $R^2$, independently of one another, are selected from the group consisting of H, $(C_1-C_{24})$-alkyl, $(C_3-C_8)$-cycloalkyl, $(C_2-C_7)$-heterocycloalkyl, $(C_6-C_{14})$-aryl or $(C_3-C_{13})$-heteroaryl, where both the radicals R with $R^1$, R with $R^2$ and also $R^1$ with $R^2$, independently of one another, form a saturated or mono- or polyunsaturated $(C_2-C_{18})$-alkylene or $(C_2-C_{18})$-heteroalkylene bridge, such that an aliphatic or aromatic ring having in total 3-20 ring atoms is formed,
or
ii. carboxylic acid diamide of the general formula (II)

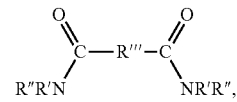

where
R''' is selected from the group consisting of divalent $(C_1-C_{24})$-alkyl radicals, $(C_3-C_{20})$-cycloalkyl radicals, $(C_2-C_{13})$-heterocycloalkyl radicals, $(C_6-C_{14})$-aryl radicals or $(C_3-C_{13})$-heteroaryl radicals; and
R' and R'', independently of one another, are selected from the group consisting of H, $(C_1-C_{24})$-alkyl, $(C_1-C_{24})$-heteroalkyl, $(C_3-C_8)$-cycloalkyl, $(C_2-C_7)$-heterocycloalkyl, $(C_6-C_{14})$-aryl or $(C_3-C_{13})$-heteroaryl, where the radicals R' with R'' can together form a saturated or mono- or polyunsaturated $(C_2-C_{18})$-alkylene or $(C_2-C_{18})$-heteroalkylene bridge, such that an aliphatic or aromatic ring having in total 3-20 ring atoms is formed,
or
iii. di-, tri- or polypeptide, or
iv. peptide amide with carboxy-terminal amide function with an alkylating agent,
b) Addition of a hydrogenation catalyst to the reaction mixture, where the molar ratio of hydrogenation catalyst to carboxylic acid amide or carboxylic acid diamide or di-, tri- or polypeptide or peptide amide is in a range of from 1:10 to 1:100 000,
c) Reaction of the reaction mixture with hydrogen, where a hydrogen pressure of from 0.1 bar to 200 bar is established and where a temperature in a range of from 0° C. to 250° C. is established.

In the context of the present invention, the term amines refers to all compounds which have the following structural unit

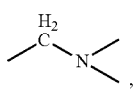

it being unimportant which further functional groups the compound has. In particular, amines are to be understood as meaning the reaction products which are formed by the hydrogenation of amide functions:

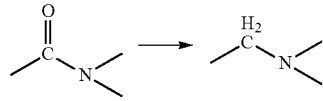

In the context of the present invention, the term carboxylic acid amide refers to compounds of the general formula (I)

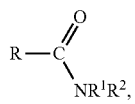

where

R is selected from the group consisting of H, $(C_1-C_{24})$-alkyl, $(C_3-C_{20})$-cycloalkyl, $(C_2-C_{13})$-heterocycloalkyl, $(C_6-C_{14})$-aryl, $(C_3-C_{13})$-heteroaryl and the acid radical of an amino acid selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine; and $R^1$ and $R^2$, independently of one another, are selected from the group consisting of H, $(C_1-C_{24})$-alkyl, $(C_3-C_8)$-cycloalkyl, $(C_2-C_7)$-heterocycloalkyl, $(C_6-C_{14})$-aryl or $(C_3-C_{13})$-heteroaryl, where both the radicals R with $R^1$, R with $R^2$ and also $R^1$ with $R^2$, independently of one another, form a saturated or mono- or polyunsaturated $(C_2-C_{18})$-alkylene or $(C_2-C_{18})$-heteroalkylene bridge, such that an aliphatic or aromatic ring having in total 3-20 ring atoms is formed.

R is preferably selected from the group consisting of H, $(C_1-C_{24})$-alkyl, phenyl, and the acid radical of an amino acid selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine; R is particularly preferably selected from H, methyl, ethyl, n-propyl, n-butyl, isobutyl, n-pentyl, n-hexyl, cyclohexyl, n-heptyl, n-octyl, phenyl, pyridyl, naphthyl, —$C_2H_4PO(OEt)_2$, —$C_8H_{16}$—CH=$CH_2$, —COOEt, N-Boc-aminomethyl, N-Boc-1-aminoethyl, N-Boc-1-amino-2-methylpropyl, N-Boc-1-amino-3-methylbutyl, N-Boc-1-amino-3-methylthiopropyl, N-Boc-1-amino-2-phenylethyl and N-Boc-pyrrolidinyl.

$R^1$ and $R^2$ are preferably selected from the group consisting of hydrogen, methyl, ethyl, n-propyl, isopropyl, n-butyl, isobutyl, n-pentyl, n-hexyl, n-heptyl, n-octyl, and phenyl.

A ring is preferably formed between the radicals R and $R^1$ or $R^1$ and $R^2$, where the ring is preferably aliphatic and has the alkylene groups propanedi-1,3-yl, butanedi-1,4-yl, pentanedi-1,5-yl or hexanedi-1,6-yl, so that the ring contains in total 4, 5, 6, 7 or 8 ring atoms. Preferably formed rings are pyrrolidine, piperidine, morpholine, piperazine, homopiperidine and homopiperazine and derivatives thereof.

Preferred carboxylic acid amides can be found in Table 1.

TABLE 1

Preferred carboxylic acid amides.

| Compound | R | $R^1$ | $R^2$ |
|---|---|---|---|
| 1 | H | Methyl | Methyl |
| 2 | H | Ethyl | Ethyl |
| 3 | H | n-Propyl | n-Propyl |
| 4 | H | iso-Propyl | iso-Propyl |
| 5 | H | n-Butyl | n-Butyl |
| 6 | H | iso-Butyl | iso-Butyl |
| 7 | H | n-Pentyl | n-Pentyl |
| 8 | H | n-Hexyl | n-Hexyl |
| 9 | H | n-Heptyl | n-Heptyl |
| 10 | H | n-Octyl | n-Octyl |
| 11 | H | Phenyl | Phenyl |
| 12 | Methyl | Methyl | Methyl |
| 13 | Methyl | Ethyl | Ethyl |
| 14 | Methyl | n-Propyl | n-Propyl |
| 15 | Methyl | iso-Propyl | iso-Propyl |
| 16 | Methyl | n-Butyl | n-Butyl |
| 17 | Methyl | iso-Butyl | iso-Butyl |
| 18 | Methyl | n-Pentyl | n-Pentyl |
| 19 | Methyl | n-Hexyl | n-Hexyl |
| 20 | Methyl | n-Heptyl | n-Heptyl |
| 21 | Methyl | n-Octyl | n-Octyl |
| 22 | Methyl | Phenyl | Phenyl |
| 23 | Ethyl | Methyl | Methyl |
| 24 | Ethyl | Ethyl | Ethyl |
| 25 | Ethyl | n-Propyl | n-Propyl |
| 26 | Ethyl | iso-Propyl | iso-Propyl |
| 27 | Ethyl | n-Butyl | n-Butyl |
| 28 | Ethyl | iso-Butyl | iso-Butyl |
| 29 | Ethyl | n-Pentyl | n-Pentyl |
| 30 | Ethyl | n-Hexyl | n-Hexyl |
| 31 | Ethyl | n-Heptyl | n-Heptyl |
| 32 | Ethyl | n-Octyl | n-Octyl |
| 33 | Ethyl | Phenyl | Phenyl |
| 34 | n-Propyl | Methyl | Methyl |
| 35 | n-Propyl | Ethyl | Ethyl |
| 36 | n-Propyl | n-Propyl | n-Propyl |
| 37 | n-Propyl | iso-Propyl | iso-Propyl |
| 38 | n-Propyl | n-Butyl | n-Butyl |
| 39 | n-Propyl | iso-Butyl | iso-Butyl |
| 40 | n-Propyl | n-Pentyl | n-Pentyl |
| 41 | n-Propyl | n-Hexyl | n-Hexyl |
| 42 | n-Propyl | n-Heptyl | n-Heptyl |
| 43 | n-Propyl | n-Octyl | n-Octyl |
| 44 | n-Propyl | Phenyl | Phenyl |
| 45 | n-Butyl | Methyl | Methyl |
| 46 | n-Butyl | Ethyl | Ethyl |
| 47 | n-Butyl | n-Propyl | n-Propyl |
| 48 | n-Butyl | iso-Propyl | iso-Propyl |
| 49 | n-Butyl | n-Butyl | n-Butyl |
| 50 | n-Butyl | iso-Butyl | iso-Butyl |
| 51 | n-Butyl | n-Pentyl | n-Pentyl |
| 52 | n-Butyl | n-Hexyl | n-Hexyl |
| 53 | n-Butyl | n-Heptyl | n-Heptyl |
| 54 | n-Butyl | n-Octyl | n-Octyl |
| 55 | n-Butyl | Phenyl | Phenyl |
| 56 | iso-Butyl | Methyl | Methyl |
| 57 | iso-Butyl | Ethyl | Ethyl |
| 58 | iso-Butyl | n-Propyl | n-Propyl |
| 59 | iso-Butyl | iso-Propyl | iso-Propyl |
| 60 | iso-Butyl | n-Butyl | n-Butyl |
| 61 | iso-Butyl | iso-Butyl | iso-Butyl |
| 62 | iso-Butyl | n-Pentyl | n-Pentyl |
| 63 | iso-Butyl | n-Hexyl | n-Hexyl |
| 64 | iso-Butyl | n-Heptyl | n-Heptyl |
| 65 | iso-Butyl | n-Octyl | n-Octyl |
| 66 | iso-Butyl | Phenyl | Phenyl |
| 67 | n-Pentyl | Methyl | Methyl |
| 68 | n-Pentyl | Ethyl | Ethyl |
| 69 | n-Pentyl | n-Propyl | n-Propyl |
| 70 | n-Pentyl | iso-Propyl | iso-Propyl |
| 71 | n-Pentyl | n-Butyl | n-Butyl |

TABLE 1-continued

Preferred carboxylic acid amides.

| Compound | R | R¹ | R² |
|---|---|---|---|
| 72 | n-Pentyl | iso-Butyl | iso-Butyl |
| 73 | n-Pentyl | n-Pentyl | n-Pentyl |
| 74 | n-Pentyl | n-Hexyl | n-Hexyl |
| 75 | n-Pentyl | n-Heptyl | n-Heptyl |
| 76 | n-Pentyl | n-Octyl | n-Octyl |
| 77 | n-Pentyl | Phenyl | Phenyl |
| 78 | n-Hexyl | Methyl | Methyl |
| 79 | n-Hexyl | Ethyl | Ethyl |
| 80 | n-Hexyl | n-Propyl | n-Propyl |
| 81 | n-Hexyl | iso-Propyl | iso-Propyl |
| 82 | n-Hexyl | n-Butyl | n-Butyl |
| 83 | n-Hexyl | iso-Butyl | iso-Butyl |
| 84 | n-Hexyl | n-Pentyl | n-Pentyl |
| 85 | n-Hexyl | n-Hexyl | n-Hexyl |
| 86 | n-Hexyl | n-Heptyl | n-Heptyl |
| 87 | n-Hexyl | n-Octyl | n-Octyl |
| 88 | n-Hexyl | Phenyl | Phenyl |
| 89 | Cyclohexyl | Methyl | Methyl |
| 90 | Cyclohexyl | Ethyl | Ethyl |
| 91 | Cyclohexyl | n-Propyl | n-Propyl |
| 92 | Cyclohexyl | iso-Propyl | iso-Propyl |
| 93 | Cyclohexyl | n-Butyl | n-Butyl |
| 94 | Cyclohexyl | iso-Butyl | iso-Butyl |
| 95 | Cyclohexyl | n-Pentyl | n-Pentyl |
| 96 | Cyclohexyl | n-Hexyl | n-Hexyl |
| 97 | Cyclohexyl | n-Heptyl | n-Heptyl |
| 98 | Cyclohexyl | n-Octyl | n-Octyl |
| 99 | Cyclohexyl | Phenyl | Phenyl |
| 100 | n-Heptyl | Methyl | Methyl |
| 101 | n-Heptyl | Ethyl | Ethyl |
| 102 | n-Heptyl | n-Propyl | n-Propyl |
| 103 | n-Heptyl | iso-Propyl | iso-Propyl |
| 104 | n-Heptyl | n-Butyl | n-Butyl |
| 105 | n-Heptyl | iso-Butyl | iso-Butyl |
| 106 | n-Heptyl | n-Pentyl | n-Pentyl |
| 107 | n-Heptyl | n-Hexyl | n-Hexyl |
| 108 | n-Heptyl | n-Heptyl | n-Heptyl |
| 109 | n-Heptyl | n-Octyl | n-Octyl |
| 110 | n-Heptyl | Phenyl | Phenyl |
| 111 | n-Octyl | Methyl | Methyl |
| 112 | n-Octyl | Ethyl | Ethyl |
| 113 | n-Octyl | n-Propyl | n-Propyl |
| 114 | n-Octyl | iso-Propyl | iso-Propyl |
| 115 | n-Octyl | n-Butyl | n-Butyl |
| 116 | n-Octyl | iso-Butyl | iso-Butyl |
| 117 | n-Octyl | n-Pentyl | n-Pentyl |
| 118 | n-Octyl | n-Hexyl | n-Hexyl |
| 119 | n-Octyl | n-Heptyl | n-Heptyl |
| 120 | n-Octyl | n-Octyl | n-Octyl |
| 121 | n-Octyl | Phenyl | Phenyl |
| 122 | Phenyl | Methyl | Methyl |
| 123 | Phenyl | Ethyl | Ethyl |
| 124 | Phenyl | n-Propyl | n-Propyl |
| 125 | Phenyl | iso-Propyl | iso-Propyl |
| 126 | Phenyl | n-Butyl | n-Butyl |
| 127 | Phenyl | iso-Butyl | iso-Butyl |
| 128 | Phenyl | n-Pentyl | n-Pentyl |
| 129 | Phenyl | n-Hexyl | n-Hexyl |
| 130 | Phenyl | n-Heptyl | n-Heptyl |
| 131 | Phenyl | n-Octyl | n-Octyl |
| 132 | Phenyl | Phenyl | Phenyl |
| 133 | Pyridyl | Methyl | Methyl |
| 134 | Pyridyl | Ethyl | Ethyl |
| 135 | Pyridyl | n-Propyl | n-Propyl |
| 136 | Pyridyl | iso-Propyl | iso-Propyl |
| 137 | Pyridyl | n-Butyl | n-Butyl |
| 138 | Pyridyl | iso-Butyl | iso-Butyl |
| 139 | Pyridyl | n-Pentyl | n-Pentyl |
| 140 | Pyridyl | n-Hexyl | n-Hexyl |
| 141 | Pyridyl | n-Heptyl | n-Heptyl |
| 142 | Pyridyl | n-Octyl | n-Octyl |
| 143 | Pyridyl | Phenyl | Phenyl |
| 144 | Naphthyl | Methyl | Methyl |
| 145 | Naphthyl | Ethyl | Ethyl |
| 146 | Naphthyl | n-Propyl | n-Propyl |
| 147 | Naphthyl | iso-Propyl | iso-Propyl |
| 148 | Naphthyl | n-Butyl | n-Butyl |
| 149 | Naphthyl | iso-Butyl | iso-Butyl |
| 150 | Naphthyl | n-Pentyl | n-Pentyl |
| 151 | Naphthyl | n-Hexyl | n-Hexyl |
| 152 | Naphthyl | n-Heptyl | n-Heptyl |
| 153 | Naphthyl | n-Octyl | n-Octyl |
| 154 | Naphthyl | Phenyl | Phenyl |
| 155 | —$C_2H_4PO(OEt)_2$ | Methyl | Methyl |
| 156 | —$C_8H_{16}$—CH=$CH_2$ (1-Decenyl?) | Methyl | Methyl |
| 157 | —C(=O)OEt | Methyl | Methyl |
| 158 | —$(CH_2)_2$—C(=O)$NMe_2$ | Methyl | Methyl |
| 159 | H | | —$(CH_2)_3$— |
| 160 | Methyl | | —$(CH_2)_3$— |
| 161 | Ethyl | | —$(CH_2)_3$— |
| 162 | Propyl | | —$(CH_2)_3$— |
| 163 | Butyl | | —$(CH_2)_3$— |
| 164 | n-Pentyl | | —$(CH_2)_3$— |
| 165 | n-Hexyl | | —$(CH_2)_3$— |
| 166 | Cyclohexyl | | —$(CH_2)_3$— |
| 167 | n-Heptyl | | —$(CH_2)_3$— |
| 168 | n-Octyl | | —$(CH_2)_3$— |
| 169 | Pyridyl | | —$(CH_2)_3$— |
| 170 | Naphthyl | | —$(CH_2)_3$— |
| 171 | Phenyl | | —$(CH_2)_3$— |
| 172 | H | | —$(CH_2)_4$— |
| 173 | Methyl | | —$(CH_2)_4$— |
| 174 | Ethyl | | —$(CH_2)_4$— |
| 175 | Propyl | | —$(CH_2)_4$— |
| 176 | Butyl | | —$(CH_2)_4$— |
| 177 | n-Pentyl | | —$(CH_2)_4$— |
| 178 | n-Hexyl | | —$(CH_2)_4$— |
| 179 | Cyclohexyl | | —$(CH_2)_4$— |
| 180 | n-Heptyl | | —$(CH_2)_4$— |
| 181 | n-Octyl | | —$(CH_2)_4$— |
| 182 | Pyridyl | | —$(CH_2)_4$— |
| 183 | Naphthyl | | —$(CH_2)_4$— |
| 184 | Phenyl | | —$(CH_2)_4$— |
| 185 | H | | —$(CH_2)_5$— |
| 186 | Methyl | | —$(CH_2)_5$— |
| 187 | Ethyl | | —$(CH_2)_5$— |
| 188 | Propyl | | —$(CH_2)_5$— |
| 189 | Butyl | | —$(CH_2)_5$— |
| 190 | n-Pentyl | | —$(CH_2)_5$— |
| 191 | n-Hexyl | | —$(CH_2)_5$— |
| 192 | Cyclohexyl | | —$(CH_2)_5$— |
| 193 | n-Heptyl | | —$(CH_2)_5$— |
| 194 | n-Octyl | | —$(CH_2)_5$— |
| 195 | Pyridyl | | —$(CH_2)_5$— |
| 196 | Naphthyl | | —$(CH_2)_5$— |
| 197 | Phenyl | | —$(CH_2)_5$— |
| 198 | H | | —$(CH_2)_6$— |
| 199 | Methyl | | —$(CH_2)_6$— |
| 200 | Ethyl | | —$(CH_2)_6$— |
| 201 | Butyl | | —$(CH_2)_6$— |
| 202 | Butyl | | —$(CH_2)_6$— |
| 203 | n-Pentyl | | —$(CH_2)_6$— |
| 204 | n-Hexyl | | —$(CH_2)_6$— |
| 205 | Cyclohexyl | | —$(CH_2)_6$— |
| 206 | n-Heptyl | | —$(CH_2)_6$— |
| 207 | n-Octyl | | —$(CH_2)_6$— |
| 208 | Pyridyl | | —$(CH_2)_6$— |
| 209 | Naphthyl | | —$(CH_2)_6$— |
| 210 | Phenyl | | —$(CH_2)_6$— |
| 211 | | —$(CH_2)_3$— | —$(CH_2)_2$—CN |
| 212 | | —$(CH_2)_3$— | H |
| 213 | | —$(CH_2)_3$— | Methyl |
| 214 | | —$(CH_2)_4$— | H |
| 215 | | —$(CH_2)_4$— | Methyl |
| 216 | | —$(CH_2)_5$— | H |
| 217 | | —$(CH_2)_5$— | Methyl |
| 218 | | —C(=O)—O—$(CH_2)_2$— | H |
| 219 | | —C(=O)—O—$(CH_2)_2$— | Methyl |
| 220 | | —$(CH_2)_2$—NH—$(CH_2)_2$— | H |
| 221 | | —$(CH_2)_2$—NH—$(CH_2)_2$— | Methyl |

TABLE 1-continued

Preferred carboxylic acid amides.

| Compound | R | R$^1$ | R$^2$ |
|---|---|---|---|
| 222 | —(CH$_2$)$_3$—NH—(CH$_2$)$_2$— | | H |
| 223 | —(CH$_2$)$_3$—NH—(CH$_2$)$_2$— | | Methyl |

In the context of the present invention, the term carboxylic acid diamide refers to compounds of the general formula (II)

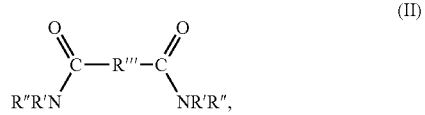

(II)

where
R''' is selected from the group consisting of divalent (C$_1$-C$_{24}$)-alkyl radicals, (C$_3$-C$_{20}$)-cycloalkyl radicals, (C$_2$-C$_{13}$)-heterocycloalkyl radicals, (C$_6$-C$_{14}$)-aryl radicals or (C$_3$-C$_{13}$)-heteroaryl radicals; and
R' and R'', independently of one another, are selected from the group consisting of H, (C$_1$-C$_{24}$)-alkyl, (C$_1$-C$_{24}$)-heteroalkyl, (C$_3$-C$_8$)-cycloalkyl, (C$_2$-C$_7$)-heterocycloalkyl, (C$_6$-C$_{14}$)-aryl or (C$_3$-C$_{13}$)-heteroaryl, where the radicals R' with R'' can together form a saturated or mono- or polyunsaturated (C$_2$-C$_{18}$)-alkylene or (C$_2$-C$_{18}$)-heteroalkylene bridge, such that an aliphatic or aromatic ring having in total 3-20 ring atoms is formed.
R''' is preferably selected from divalent (C$_1$-C$_{24}$)-alkyl radicals, with the group consisting of methylene, ethylene, n-propylene, n-butylene, n-pentylene, and n-hexylene being preferred.
R' and R'' are preferably independently selected from the group consisting of hydrogen, methyl, ethyl, n-propyl, isopropyl, n-butyl, isobutyl, n-pentyl, n-hexyl, n-heptyl, n-octyl, butanedi-1,4-yl, pentanedi-1,5-yl, hexanedi-1,6-yl and phenyl.
A ring between the radicals R' and R'' is preferably aliphatic and has in total 5, 6 or 7 ring atoms. Preferably formed rings are pyrrolidine, piperidine, morpholine, piperazine, homopiperidine and homopiperazine and derivatives thereof.
Preferred carboxylic acid diamides are N,N,N',N'-tetramethylsuccinic acid diamide, N,N,N',N'-tetramethyladipic acid diamide, N,N,N',N'-tetramethylsuberic acid diamide, N,N,N',N'-tetramethylterephthalic acid diamide and sarcosine anhydride.

In the context of the present invention, the term di-, tri- or polypeptide refers to compounds which contain a peptide bond between amino acids.

A dipeptide here refers to the compound between two amino acids AS$^1$-AS$^2$, a tripeptide refers to the compound between three amino acids AS$^1$-AS$^2$-AS$^3$ and a polypeptide refers to the compound between four to more than 100 amino acids. The amino acids AS$^1$, AS$^2$ and AS$^3$ can in each case independently of one another be selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, with the D- and L-enantiomers being included. During the condensation of amino acids, the carboxyl group of the one amino acid reacts formally with the elimination of water with the amino group of the other amino acid to give the acid amide grouping —C(=O)—NH, the newly linked amide bond between the carbon of the carbonyl group and the nitrogen atom is called a peptide bond.

The free amino group at one end of the peptide is called the N terminus, the free carboxyl group at the other end is called the C terminus or carboxy terminus. The carboxy terminus is preferably alkylated or silylated, with alkylation preferably being with methyl or ethyl, MeOCH$_2$—, tetrahydropyranyl (THP), PhCOCH$_2$—, t-Bu, allyl, benzyl(Bn), Ph$_2$CH— or silylation is with Me$_3$Si— or t-BuMe$_2$Si-(TBDMS); the N terminus is preferably provided with a protective group, where the protective group is preferably selected from the following group consisting of Boc, Cbz, Fmoc and Alloc, where Boc=tert-butyloxycarbonyl, Cbz=benzyloxycarbonyl, Fmoc=fluorenylmethyleneoxycarbonyl, Alloc=allyloxycarbonyl.

Examples of dipeptides can be found in Table 2.

TABLE 2

Preferred dipeptides AS$^1$-AS$^2$, where the amino acid AS$^1$ is given in the first column in the 3-letter code and the amino acid AS$^2$ is given in the first line in the 3-letter code, and where in each case the D- and L-enantiomers are included.

| | Ala | Arg | Asn | Asp | Cys | Gln | Glu | His | Ile | Leu | Lys | Met | Phe | Pro | Ser | Thr | Trp | Tyr | Val |
|---|---|---|---|---|---|---|---|---|---|---|---|---|---|---|---|---|---|---|---|
| Ala | x | x | x | x | x | x | x | x | x | x | x | x | x | x | x | x | x | x | x |
| Arg | x | x | x | x | x | x | x | x | x | x | x | x | x | x | x | x | x | x | x |
| Asn | x | x | x | x | x | x | x | x | x | x | x | x | x | x | x | x | x | x | x |
| Asp | x | x | x | x | x | x | x | x | x | x | x | x | x | x | x | x | x | x | x |
| Cys | x | x | x | x | x | x | x | x | x | x | x | x | x | x | x | x | x | x | x |
| Gln | x | x | x | x | x | x | x | x | x | x | x | x | x | x | x | x | x | x | x |
| Glu | x | x | x | x | x | x | x | x | x | x | x | x | x | x | x | x | x | x | x |
| Gly | x | x | x | x | x | x | x | x | x | x | x | x | x | x | x | x | x | x | x |
| His | x | x | x | x | x | x | x | x | x | x | x | x | x | x | x | x | x | x | x |
| Ile | x | x | x | x | x | x | x | x | x | x | x | x | x | x | x | x | x | x | x |
| Leu | x | x | x | x | x | x | x | x | x | x | x | x | x | x | x | x | x | x | x |
| Lys | x | x | x | x | x | x | x | x | x | x | x | x | x | x | x | x | x | x | x |
| Met | x | x | x | x | x | x | x | x | x | x | x | x | x | x | x | x | x | x | x |
| Phe | x | x | x | x | x | x | x | x | x | x | x | x | x | x | x | x | x | x | x |
| Pro | x | x | x | x | x | x | x | x | x | x | x | x | x | x | x | x | x | x | x |
| Ser | x | x | x | x | x | x | x | x | x | x | x | x | x | x | x | x | x | x | x |
| Thr | x | x | x | x | x | x | x | x | x | x | x | x | x | x | x | x | x | x | x |
| Trp | x | x | x | x | x | x | x | x | x | x | x | x | x | x | x | x | x | x | x |

TABLE 2-continued

Preferred dipeptides $AS^1$-$AS^2$, where the amino acid $AS^1$ is given in the first column in the 3-letter code and the amino acid $AS^2$ is given in the first line in the 3-letter code, and where in each case the D- and L-enantiomers are included.

|     | Ala | Arg | Asn | Asp | Cys | Gln | Glu | His | Ile | Leu | Lys | Met | Phe | Pro | Ser | Thr | Trp | Tyr | Val |
|-----|-----|-----|-----|-----|-----|-----|-----|-----|-----|-----|-----|-----|-----|-----|-----|-----|-----|-----|-----|
| Tyr | x   | x   | x   | x   | x   | x   | x   | x   | x   | x   | x   | x   | x   | x   | x   | x   | x   | x   | x   |
| Val | x   | x   | x   | x   | x   | x   | x   | x   | x   | x   | x   | x   | x   | x   | x   | x   | x   | x   | x   |

In the context of the present invention, the term peptide amide with carboxy-terminal amide function refers to a di-, tri- or polypeptide which has on the carboxy terminus an amide function-$NR^1R^2$, where $R^1$ and $R^2$ are selected independently of one another from H, $(C_1-C_{24})$-alkyl, $(C_3-C_8)$-cycloalkyl, $(C_2-C_7)$-heterocycloalkyl, $(C_6-C_{14})$-aryl and $(C_3-C_{13})$-heteroaryl.

A $(C_1-C_n)$-alkyl radical is understood as meaning either linear or branched alkyl radicals having 1 to n carbon atoms. In the case of branched alkyl radicals, the branching can occur on any desired carbon atom.

Preferred $(C_1-C_n)$-alkyl radicals are methyl, ethyl, n-propyl, isopropyl, n-butyl, isobutyl, sec-butyl, n-pentyl, isopentyl, n-hexyl, n-heptyl, n-octyl, n-nonyl, n-decyl, n-dodecyl and n-octadecyl.

The $(C_1-C_n)$-alkyl radical can be substituted or unsubstituted; it is preferably unsubstituted.

A $(C_1-C_n)$-heteroalkyl radical is understood as meaning either linear or branched alkyl radicals having 1 to n carbon atoms, where 1 or 2 carbon atoms are replaced by heteroatoms selected from the group N, O, P. In the case of branched heteroalkyl radicals, the branching can occur on any desired carbon atom. The $(C_1-C_n)$-heteroalkyl radical can be substituted or unsubstituted; it is preferably unsubstituted.

A $(C_3-C_n)$-cycloalkyl radical refers to a mono-, bi- or tricyclic, aliphatic system of in total 3 to n carbon atoms, where each ring can be three-, four-, five-, six- or seven-membered. Preference is given to $(C_6-C_{12})$-cycloalkyl radicals. Particularly preferred $(C_3-C_n)$-cycloalkyl radicals are cyclopropyl, cyclobutyl, cyclopentyl, cyclohexyl, cycloheptyl and 1-adamantyl, 9-fluorenyl.

The $(C_3-C_n)$-cycloalkyl radical can be substituted or unsubstituted; it is preferably unsubstituted.

A $(C_2-C_n)$-heterocycloalkyl radical refers to a mono-, bi- or tricyclic, aliphatic system of in total 2 to n carbon atoms, where each ring can be three-, four-, five-, six- or seven-membered, and where the number of heteroatoms, selected from the group N, O, and S, is 1 or 2 and the heteroatoms are identical or different. Preferred heterocycloalkyl radicals are 2-, 3-tetrahydrofuryl, 1-, 2-,3-pyrrolidinyl, 1-, 2-, 3-, 4-piperidinyl, 1-, 2-piperazinyl, 1-, 2-, 3-morpholinyl, tetrahydropyranyl-2 or -3 and 2,3-dihydrobenzothiophenyl-2 or -3.

The $(C_2-C_n)$-heterocycloalkyl radical can be substituted or unsubstituted; it is preferably unsubstituted.

A $(C_6-C_n)$-aryl radical refers to a mono-, bi- and tricyclic aromatic system with 6 to n carbon atoms, where each ring can in each case be five-, six- or seven-membered. Preferred $(C_6-C_n)$-aryl radicals are phenyl, naphthyl, anthryl, phenanthryl, biphenyl.

The $(C_6-C_n)$-aryl radical can be substituted or unsubstituted; it is preferably unsubstituted.

A $(C_3-C_n)$-heteroaryl radical refers to a mono-, bi- or tricyclic, aromatic system of in total 3 to n carbon atoms, where each ring can in each case be five-, six- or seven-membered, and where the number of heteroatoms, selected from the group N, O, and S, is 1 or 2 and the heteroatoms are identical or different. Preferred $(C_2-C_n)$-heteroaryl radicals are 2-, 3-furyl, 2-, 3-pyrrolyl, 2-, 4-, 5-imidazolyl, 2-, 3-thienyl, 2-, 3-, 4-pyridyl, 2-, 3-, 4-, 5-, 6-, 7-indolyl, 3-, 4-, 5-pyrazolyl, 2-, 4-, 5-, 6-pyrimidinyl, acridinyl, quinolinyl, phenanthridinyl, benzothienyl.

The $(C_3-C_n)$-heteroalkyl radical can be substituted or unsubstituted; it is preferably unsubstituted.

Substituents are selected from the group consisting of halogens such as F, Cl, Br, I, and heteroatom-containing functional groups which contain one or more atoms selected from the group consisting of N, O, P, S, or Si, where single and multiple substitution is possible. Examples of heteroatom-containing functional groups are carbonyl, carboxyl, sulphonate, phosphonate, hydroxyl, amino, ammonium groups such as —OH,
—$(C_1-C_8)$-alkyloxy
—COOH,
—NH($\{C_1-C_8\}$-acyl),
—NH($\{C_1-C_8\}$-acyloxy)
—N(($C_1-C_{20}$)-alkyl) ($\{C_1-C_8\}$-acyl),
—N($\{C_6-C_{14}\}$-aryl) ($\{C_1-C_8\}$-acyl),
—N($\{C_6-C_{14}\}$-aralkyl) ($\{C_1-C_8\}$-acyl),
—N($\{C_1-C_8\}$-acyl)$_2$,
—$NH_3^+$,
—NH($\{C_1-C_{20}\}$-alkyl)$_2^+$,
—NH($\{C_6-C_{14}\}$-aryl)$_2^+$,
—NH($\{C_6-C_{14}\}$-aralkyl)$_2^+$,
—NH($\{C_1-C_{20}\}$-alkyl) ($\{C_6-C_{14}\}$-aryl)$^+$,
—N($\{C_6-C_{14}\}$-aryl) ($\{C_1-C_{20}\}$-alkyl)$_+$,
—N($\{C_6-C_{14}\}$-aryl)$_2$ ($\{C_1-C_{20}\}$-alkyl)$^+$,
—O—C(=O)—O—$\{C_1-C_{20}\}$-alkyl,
—O—C(=O)—O—$\{C_6-C_{14}\}$-aryl,
—O—C(=O)—O—$\{C_6-C_{14}\}$-aralkyl,
—NH—C(=O)—O—$\{C_1-C_{20}\}$-alkyl,
—NH—C(=O)—O—$\{C_6-C_{14}\}$-aryl,
—NH—C(=O)—O—$\{C_6-C_{14}\}$-aralkyl,
—O—C(=O)—NH—$\{C_1-C_{20}\}$-alkyl,
—O—C(=O)—NH—$\{C_6-C_{14}\}$-aryl,
—O—C(=O)—NH—$\{C_6-C_{14}\}$-aralkyl,
—CN,
—$SO_2$—O—$\{C_1-C_{20}\}$-alkyl,
—$SO_2$—O—$\{C_6-C_{14}\}$-aryl,
—$SO_2$—O—$\{C_6-C_{14}\}$-aralkyl,
—$SO_2$—$\{C_1-C_{20}\}$-alkyl,
—$SO_2$—$\{C_6-C_{14}\}$-aryl,
—$SO_2$—$\{C_6-C_{14}\}$-aralkyl,
—SO—$\{C_1-C_{20}\}$-alkyl,
—SO—$\{C_6-C_{14}\}$-aryl,
—SO—$\{C_6-C_{14}\}$-aralkyl,
—Si($\{C_1-C_{20}\}$-alkyl)$_3$,
—Si($\{C_6-C_{14}\}$-aryl)$_3$,
—Si($\{C_6-C_{14}\}$-aryl) ($\{C_1-C_{20}\}$-alkyl)$_2$,
—Si($\{C_6-C_{14}\}$-aryl)$_2$ ($\{C_1-C_{20}\}$-alkyl),
—$\{C_1-C_{20}\}$-perfluoroalkyl,
—PO(O—$\{C_1-C_{20}\}$-alkyl)$_2$,
—PO(O—$\{C_6-C_{14}\}$-aryl)$_2$, —PO(O—{$C_1$-$C_{20}$}-alkyl) (O—{$C_6$-$C_{14}$}-aryl),
—PO({$C_1$-$C_{20}$}-alkyl)$_2$,
—PO({$C_6$-$C_{14}$}-aryl)$_2$,
—PO({$C_1$-$C_{20}$}-alkyl) ({$C_6$-$C_{14}$}-aryl).

In the context of the present invention, ($C_1$-$C_n$)-alkyloxy is defined as linear or branched ($C_1$-$C_n$)-alkyl group with 1 to n carbon atoms, with the proviso that this is bonded to the molecule carrying this group via an oxygen atom.

In the context of the present invention, ($C_1$-$C_n$)-acyl is defined as a group with the general structure R—(C=O)— with in total 1 to n carbon atoms, where R is selected from the group consisting of H, ($C_1$-$C_{n-1}$)-alkyl, ($C_1$-$C_{n-1}$)-alkenyl, ($C_6$-$C_{n-1}$)-aryl, ($C_6$-$C_{n-1}$)-heteroaryl and ($C_2$-$C_{n-1}$)-alkynyl.

In the context of the present invention, ($C_1$-$C_n$)-acyloxy is a group with the general structure R'—(C=O)O— with in total 1 to n carbon atoms, where R' is selected from the group consisting of H, ($C_1$-$C_{n-1}$)-alkyl, ($C_1$-$C_{n-1}$)-alkenyl, ($C_6$-$C_{n-1}$)-aryl, ($C_6$-$C_{n-1}$)-heteroaryl and ($C_2$-$C_{n-1}$)-alkynyl.

In the context of the present invention, ($C_2$-$C_n$)-alkenyl is defined as linear or branched ($C_2$-$C_n$)-alkyl group with 2 to n carbon atoms, with the proviso that this has a C=C double bond.

In the context of the present invention, ($C_2$-$C_n$)-alkynyl is defined as linear or branched ($C_2$-$C_n$)-alkyl group with 2 to n carbon atoms, with the proviso that this has a C—C triple bond.

In the context of the present invention, ($C_6$-$C_n$)-aralkyl refers to a group which contains both an alkyl and an aryl group and has in total 6 to n carbon atoms. The aralkyl group can be bonded to the molecule carrying this group via any of its carbon atoms. A ($C_6$-$C_n$)-aralkyl group can also be substituted with at least one substituent, where the substituents independently of one another are selected from the group consisting of halogen, ($C_1$-$C_8$)-alkyl, ($C_1$-$C_8$)-alkyloxy, —$NH_2$, —NO, —$NO_2$, NH($C_1$-$C_8$)-alkyl, —N(($C_1$-$C_8$)-alkyl)$_2$, —OH, —$CF_3$, —$C_nF_{2n+1}$ (where n is an integer from 2 to 5), NH($C_1$-$C_8$)-acyl, —N(($C_1$-$C_8$)-acyl)$_2$, ($C_1$-$C_8$)-acyl, ($C_1$-$C_8$)-acyloxy, —$SO_2$—($C_1$-$C_8$)-alkyl, —$SO_2$—($C_6$-$C_{14}$)-aryl, —SO—($C_1$-$C_8$)-alkyl, —SO—($C_6$-$C_{14}$)-aryl, —PO(O—{$C_1$-$C_{20}$}-alkyl)$_2$, —PO(O—{$C_6$-$C_{14}$}-aryl)$_2$, —PO(O—{$C_1$-$C_{20}$}-alkyl) (O—{$C_6$-$C_{14}$}-aryl), —PO({$C_1$-$C_{20}$}-alkyl)$_2$, —PO({$C_6$-$C_{14}$}-aryl)$_2$, —PO({$C_1$-$C_{20}$}-alkyl) ({$C_6$-$C_{14}$}-aryl).

Alkylating agents that can be used are all compounds contemplated for this purpose by the person skilled in the art, preference being given to alkylating agents which are selected from the group consisting of alkyl halides, esters of sulphonic acid, esters of fluorosulphonic acid, esters of trifluoromethanesulphonic acid, esters of chloroformic acid, oxonium salts, dialkyl sulphates and diazomethane. Alkylating agents which are selected from the group consisting of ($Me_3O$) $BF_4$, ($Et_3O$) $BF_4$, $(MeO)_2SO_2$, $(EtO)_2SO_2$, ClCOOEt, MeI and EtI, are particularly preferred here.

The amount of alkylating agent can be freely chosen by the person skilled in the art. However, the alkylating agent is preferably used in a molar ratio in a range from 1:1 to 2:1, based on the carbonyl group(s) to be reduced.

As hydrogenation catalyst, it is possible to select all hydrogenation catalysts contemplated by the person skilled in the art for this purpose. Preference is given to using those hydrogenation catalysts which contain at least one active metal. Preferably, the active metal is one of groups VII B and/or VIII B of the Periodic Table of the Elements, with precious metals and Ni being preferred, and Ru, Rh, Pd, Pt, Re and Ni being particularly preferred. The metals can be present in the hydrogenation catalyst either (a) as they are or in the form of oxides or (b) as metal complexes.

In case (a), the metal or metal oxide can either be applied to a support or be used as particles. The support material is not limited, usually customary supports such as aluminium oxide, silicon dioxide, aluminium oxide, iron oxide, magnesium oxide, zirconium dioxide, carbon or similar supports known to the person skilled in the art in the field of hydrogenation are used. The content of metal or metal oxide on the support is selected in a range of from 1% by weight to 25% by weight, based on the total weight of the catalyst. Preferably, a content of from 1 to 5% by weight of metal or metal oxide on the support is selected.

Examples of such hydrogenation catalysts are Pt/C, Pd/C, Rh/C, Ru/C, Pd/$CaCO_3$, Pd/$Al_2O_3$, Ru/$Al_2O_3$, Rh/$Al_2O_3$, Pd/Re/C, Pt/Re/C, $RuO_2$.

In case (b), the metals can also be used in the form of metal complexes as hydrogenation catalysts. Examples thereof are metal complexes of the metals Rh, Ir or Ru, such as e.g. the Wilkinson catalyst ClRh(PPh$_3$)$_3$ or [(dppb)Rh(cod)]BF$_4$, [Ir(PCy$_3$)(C$_5$H$_5$N)(cod)]PF$_6$, [Cl$_2$Ru(PPh$_3$)$_3$] and [(dppb)Ru(metallyl)$_2$].

Preferably, the hydrogenation catalyst is selected from the group consisting of Pd/C, Pd/$Al_2O_3$, Pd/$CaCO_3$, Pt/C, Ru/$Al_2O_3$, Pd/Re/C, Pt/Re/C and [(dppb)Rh(cod)]BF$_4$. Particularly preferably, the hydrogenation catalyst is selected from the group consisting of 5% Pd/C, 5% Pd/$Al_2O_3$, 5% Pd/$CaCO_3$, 5% Pt/C, 5% Ru/$Al_2O_3$ and [(dppb) Rh (cod)] BF$_4$.

The amount of hydrogenation catalyst can be freely selected by the person skilled in the art, where the molar ratio of hydrogenation catalyst to carboxylic acid amide or carboxylic acid diamide or di-, tri- or polypeptide or peptide amide is in a range of from 1:10 to 1:100 000. Further preference is given to a range of from 1:20 to 1:10 000, particular preference being given to a range of from 1:50 to 1:2000.

In principle, the person skilled in the art is free to select the solvent that he would like to use in the process according to the invention. On account of the fact that the starting materials are often in liquid form, it is in this regard also possible to dispense with using a solvent. If, however, the use of solvents in the process according to the invention is desired, it is advantageous to use those solvents which accordingly readily dissolve the components of the reaction used and otherwise have proven to be inert towards the reaction according to the invention. Examples include polar or nonpolar solvents, in particular inter alia hydrocarbons, chlorinated hydrocarbons, ethers, esters and alcohols. Preference is given here to alkanes, haloalkanes, monohydric and polyhydric alcohols, cyclic and acyclic ethers, and esters.

Preferred solvents are those selected from the group consisting of hexane, heptane, octane, dimethyl glycol ether (DMGE), 1,4-dioxane, methyl tert-butyl ether (MTBE), tetradydrofuran (THF), ethyl acetate, isopropyl acetate, dibutyl ether, dimethyl carbonate, diethyl carbonate, dipropyl carbonate, methanol, ethanol, isopropanol, butanol, ethylene glycol, dichloromethane and 1,2-dichloroethane. Particular preference is given to methanol and ethanol.

The hydrogen pressure of the reaction is established in a range of from 0.1 to 200 bar, preferably of from 0.1 to 100 bar, and particularly preferably of from 0.1 to 60 bar.

The temperature which is to be established during the reaction can be determined by the person skilled in the art and is usually in a range of from 0° C. to 250° C. It should be high enough that the envisaged reaction proceeds in a sufficiently rapid time but be as low as possible so that the byproduct spectrum during the hydrogenation can be kept as low as possible. Preferably, a temperature from the range of from 0° C. to 120° C. is established. Particularly preferably, a temperature from the range of from 10° C. to 100° C. is established, very particularly preferably a temperature from the range of from 20° C. to 50° C. is established.

Preferred reaction conditions during the hydrogenation can be found in Table 3.

TABLE 3

Preferred reaction conditions during the hydrogenation.

| Pressure [bar] | Temperatur [° C.] | Hydroge-nation catalyst | Alkylating agent, molar ratio carbonyl: alkylating agent 1:1-1:2 | Base | Solvent | Molar ratio catalyst: starting material | Starting material |
|---|---|---|---|---|---|---|---|
| 0.1-200 | 0° C.-250° C. | [b] | [e] | Group (1) | yes | 1:20-1:10,000 | [g] |
| 0.1-200 | 0° C.-250° C. | [b] | [e] | Group (1) | no | 1:20-1:10,000 | [g] |
| 0.1-200 | 0° C.-120° C. | [b] | [e] | Group (1) | yes | 1:20-1:10,000 | [g] |
| 0.1-200 | 0° C.-120° C. | [b] | [e] | Group (1) | no | 1:20-1:10,000 | [g] |
| 0.1-200 | 10° C.-100° C. | [b] | [e] | Group (1) | yes | 1:20-1:10,000 | [g] |
| 0.1-200 | 10° C.-100° C. | [b] | [e] | Group (1) | no | 1:20-1:10,000 | [g] |
| 0.1-200 | 20° C.-50° C. | [b] | [e] | Group (1) | yes | 1:20-1:10,000 | [g] |
| 0.1-200 | 20° C.-50° C. | [b] | [e] | Group (1) | no | 1:20-1:10,000 | [g] |
| 0.1-100 | 0° C.-250° C. | [b] | [e] | Group (1) | yes | 1:20-1:10,000 | [g] |
| 0.1-100 | 0° C.-250° C. | [b] | [e] | Group (1) | no | 1:20-1:10,000 | [g] |
| 0.1-100 | 0° C.-120° C. | [b] | [e] | Group (1) | yes | 1:20-1:10,000 | [g] |
| 0.1-100 | 0° C.-120° C. | [b] | [e] | Group (1) | no | 1:20-1:10,000 | [g] |
| 0.1-100 | 10° C.-100° C. | [b] | [e] | Group (1) | yes | 1:20-1:10,000 | [g] |
| 0.1-100 | 10° C.-100° C. | [b] | [e] | Group (1) | no | 1:20-1:10,000 | [g] |
| 0.1-100 | 20° C.-50° C. | [b] | [e] | Group (1) | yes | 1:20-1:10,000 | [g] |
| 0.1-100 | 20° C.-50° C. | [b] | [e] | Group (1) | no | 1:20-1:10,000 | [g] |
| 0.1-60 | 0° C.-250° C. | [b] | [e] | Group (1) | yes | 1:20-1:10,000 | [g] |
| 0.1-60 | 0° C.-250° C. | [b] | [e] | Group (1) | no | 1:20-1:10,000 | [g] |
| 0.1-60 | 0° C.-120° C. | [b] | [e] | Group (1) | yes | 1:20-1:10,000 | [g] |
| 0.1-60 | 0° C.-120° C. | [b] | [e] | Group (1) | no | 1:20-1:10,000 | [g] |
| 0.1-60 | 10° C.-100° C. | [b] | [e] | Group (1) | yes | 1:20-1:10,000 | [g] |
| 0.1-60 | 10° C.-100° C. | [b] | [e] | Group (1) | no | 1:20-1:10,000 | [g] |
| 0.1-60 | 20° C.-50° C. | [b] | [e] | Group (1) | yes | 1:20-1:10,000 | [g] |
| 0.1-60 | 20° C.-50° C. | [b] | [e] | Group (1) | no | 1:20-1:10,000 | [g] |
| 0.1-200 | 0° C.-250° C. | [b] | [e] | Group (2) | yes | 1:20-1:10,000 | [g] |
| 0.1-200 | 0° C.-250° C. | [b] | [e] | Group (2) | no | 1:20-1:10,000 | [g] |
| 0.1-200 | 0° C.-120° C. | [b] | [e] | Group (2) | yes | 1:20-1:10,000 | [g] |
| 0.1-200 | 0° C.-120° C. | [b] | [e] | Group (2) | no | 1:20-1:10,000 | [g] |
| 0.1-200 | 10° C.-100° C. | [b] | [e] | Group (2) | yes | 1:20-1:10,000 | [g] |
| 0.1-200 | 10° C.-100° C. | [b] | [e] | Group (2) | no | 1:20-1:10,000 | [g] |
| 0.1-200 | 20° C.-50° C. | [b] | [e] | Group (2) | yes | 1:20-1:10,000 | [g] |
| 0.1-200 | 20° C.-50° C. | [b] | [e] | Group (2) | no | 1:20-1:10,000 | [g] |
| 0.1-100 | 0° C.-250° C. | [b] | [e] | Group (2) | yes | 1:20-1:10,000 | [g] |
| 0.1-100 | 0° C.-250° C. | [b] | [e] | Group (2) | no | 1:20-1:10,000 | [g] |
| 0.1-100 | 0° C.-120° C. | [b] | [e] | Group (2) | yes | 1:20-1:10,000 | [g] |
| 0.1-100 | 0° C.-120° C. | [b] | [e] | Group (2) | no | 1:20-1:10,000 | [g] |
| 0.1-100 | 10° C.-100° C. | [b] | [e] | Group (2) | yes | 1:20-1:10,000 | [g] |
| 0.1-100 | 10° C.-100° C. | [b] | [e] | Group (2) | no | 1:20-1:10,000 | [g] |
| 0.1-100 | 20° C.-50° C. | [b] | [e] | Group (2) | yes | 1:20-1:10,000 | [g] |
| 0.1-100 | 20° C.-50° C. | [b] | [e] | Group (2) | no | 1:20-1:10,000 | [g] |
| 0.1-60 | 0° C.-250° C. | [b] | [e] | Group (2) | yes | 1:20-1:10,000 | [g] |
| 0.1-60 | 0° C.-250° C. | [b] | [e] | Group (2) | no | 1:20-1:10,000 | [g] |
| 0.1-60 | 0° C.-120° C. | [b] | [e] | Group (2) | yes | 1:20-1:10,000 | [g] |
| 0.1-60 | 0° C.-120° C. | [b] | [e] | Group (2) | no | 1:20-1:10,000 | [g] |
| 0.1-60 | 10° C.-100° C. | [b] | [e] | Group (2) | yes | 1:20-1:10,000 | [g] |
| 0.1-60 | 10° C.-100° C. | [b] | [e] | Group (2) | no | 1:20-1:10,000 | [g] |
| 0.1-60 | 20° C.-50° C. | [b] | [e] | Group (2) | yes | 1:20-1:10,000 | [g] |
| 0.1-60 | 20° C.-50° C. | [b] | [e] | Group (2) | no | 1:20-1:10,000 | [g] |
| 0.1-200 | 0° C.-250° C. | [c] | [e] | Group (1) | yes | 1:20-1:10,000 | [g] |
| 0.1-200 | 0° C.-250° C. | [c] | [e] | Group (1) | no | 1:20-1:10,000 | [g] |
| 0.1-200 | 0° C.-120° C. | [c] | [e] | Group (1) | yes | 1:20-1:10,000 | [g] |
| 0.1-200 | 0° C.-120° C. | [c] | [e] | Group (1) | no | 1:20-1:10,000 | [g] |
| 0.1-200 | 10° C.-100° C. | [c] | [e] | Group (1) | yes | 1:20-1:10,000 | [g] |
| 0.1-200 | 10° C.-100° C. | [c] | [e] | Group (1) | no | 1:20-1:10,000 | [g] |
| 0.1-200 | 20° C.-50° C. | [c] | [e] | Group (1) | yes | 1:20-1:10,000 | [g] |
| 0.1-200 | 20° C.-50° C. | [c] | [e] | Group (1) | no | 1:20-1:10,000 | [g] |
| 0.1-100 | 0° C.-250° C. | [c] | [e] | Group (1) | yes | 1:20-1:10,000 | [g] |
| 0.1-100 | 0° C.-250° C. | [c] | [e] | Group (1) | no | 1:20-1:10,000 | [g] |
| 0.1-100 | 0° C.-120° C. | [c] | [e] | Group (1) | yes | 1:20-1:10,000 | [g] |
| 0.1-100 | 0° C.-120° C. | [c] | [e] | Group (1) | no | 1:20-1:10,000 | [g] |
| 0.1-100 | 10° C.-100° C. | [c] | [e] | Group (1) | yes | 1:20-1:10,000 | [g] |
| 0.1-100 | 10° C.-100° C. | [c] | [e] | Group (1) | no | 1:20-1:10,000 | [g] |
| 0.1-100 | 20° C.-50° C. | [c] | [e] | Group (1) | yes | 1:20-1:10,000 | [g] |
| 0.1-100 | 20° C.-50° C. | [c] | [e] | Group (1) | no | 1:20-1:10,000 | [g] |
| 0.1-60 | 0° C.-250° C. | [c] | [e] | Group (1) | yes | 1:20-1:10,000 | [g] |

TABLE 3-continued

Preferred reaction conditions during the hydrogenation.

| Pressure [bar] | Temperatur [° C.] | Hydroge- nation catalyst | Alkylating agent, molar ratio carbonyl: alkylating agent 1:1-1:2 | Base | Solvent | Molar ratio catalyst: starting material | Starting material |
|---|---|---|---|---|---|---|---|
| 0.1-60 | 0° C.-250° C. | [c] | [e] | Group (1) | no | 1:20-1:10,000 | [g] |
| 0.1-60 | 0° C.-120° C. | [c] | [e] | Group (1) | yes | 1:20-1:10,000 | [g] |
| 0.1-60 | 0° C.-120° C. | [c] | [e] | Group (1) | no | 1:20-1:10,000 | [g] |
| 0.1-60 | 10° C.-100° C. | [c] | [e] | Group (1) | yes | 1:20-1:10,000 | [g] |
| 0.1-60 | 10° C.-100° C. | [c] | [e] | Group (1) | no | 1:20-1:10,000 | [g] |
| 0.1-60 | 20° C.-50° C. | [c] | [e] | Group (1) | yes | 1:20-1:10,000 | [g] |
| 0.1-60 | 20° C.-50° C. | [c] | [e] | Group (1) | no | 1:20-1:10,000 | [g] |
| 0.1-200 | 0° C.-250° C. | [c] | [e] | Group (2) | yes | 1:20-1:10,000 | [g] |
| 0.1-200 | 0° C.-250° C. | [c] | [e] | Group (2) | no | 1:20-1:10,000 | [g] |
| 0.1-200 | 0° C.-120° C. | [c] | [e] | Group (2) | yes | 1:20-1:10,000 | [g] |
| 0.1-200 | 0° C.-120° C. | [c] | [e] | Group (2) | no | 1:20-1:10,000 | [g] |
| 0.1-200 | 10° C.-100° C. | [c] | [e] | Group (2) | yes | 1:20-1:10,000 | [g] |
| 0.1-200 | 10° C.-100° C. | [c] | [e] | Group (2) | no | 1:20-1:10,000 | [g] |
| 0.1-200 | 20° C.-50° C. | [c] | [e] | Group (2) | yes | 1:20-1:10,000 | [g] |
| 0.1-200 | 20° C.-50° C. | [c] | [e] | Group (2) | no | 1:20-1:10,000 | [g] |
| 0.1-100 | 0° C.-250° C. | [c] | [e] | Group (2) | yes | 1:20-1:10,000 | [g] |
| 0.1-100 | 0° C.-250° C. | [c] | [e] | Group (2) | no | 1:20-1:10,000 | [g] |
| 0.1-100 | 0° C.-120° C. | [c] | [e] | Group (2) | yes | 1:20-1:10,000 | [g] |
| 0.1-100 | 0° C.-120° C. | [c] | [e] | Group (2) | no | 1:20-1:10,000 | [g] |
| 0.1-100 | 10° C.-100° C. | [c] | [e] | Group (2) | yes | 1:20-1:10,000 | [g] |
| 0.1-100 | 10° C.-100° C. | [c] | [e] | Group (2) | no | 1:20-1:10,000 | [g] |
| 0.1-100 | 20° C.-50° C. | [c] | [e] | Group (2) | yes | 1:20-1:10,000 | [g] |
| 0.1-100 | 20° C.-50° C. | [c] | [e] | Group (2) | no | 1:20-1:10,000 | [g] |
| 0.1-60 | 0° C.-250° C. | [c] | [e] | Group (2) | yes | 1:20-1:10,000 | [g] |
| 0.1-60 | 0° C.-250° C. | [c] | [e] | Group (2) | no | 1:20-1:10,000 | [g] |
| 0.1-60 | 0° C.-120° C. | [c] | [e] | Group (2) | yes | 1:20-1:10,000 | [g] |
| 0.1-60 | 0° C.-120° C. | [c] | [e] | Group (2) | no | 1:20-1:10,000 | [g] |
| 0.1-60 | 10° C.-100° C. | [c] | [e] | Group (2) | yes | 1:20-1:10,000 | [g] |
| 0.1-60 | 10° C.-100° C. | [c] | [e] | Group (2) | no | 1:20-1:10,000 | [g] |
| 0.1-60 | 20° C.-50° C. | [c] | [e] | Group (2) | yes | 1:20-1:10,000 | [g] |
| 0.1-60 | 20° C.-50° C. | [c] | [e] | Group (2) | no | 1:20-1:10,000 | [g] |
| 0.1-200 | 0° C.-250° C. | [d] | [e] | Group (1) | yes | 1:20-1:10,000 | [g] |
| 0.1-200 | 0° C.-250° C. | [d] | [e] | Group (1) | no | 1:20-1:10,000 | [g] |
| 0.1-200 | 0° C.-120° C. | [d] | [e] | Group (1) | yes | 1:20-1:10,000 | [g] |
| 0.1-200 | 0° C.-120° C. | [d] | [e] | Group (1) | no | 1:20-1:10,000 | [g] |
| 0.1-200 | 10° C.-100° C. | [d] | [e] | Group (1) | yes | 1:20-1:10,000 | [g] |
| 0.1-200 | 10° C.-100° C. | [d] | [e] | Group (1) | no | 1:20-1:10,000 | [g] |
| 0.1-200 | 20° C.-50° C. | [d] | [e] | Group (1) | yes | 1:20-1:10,000 | [g] |
| 0.1-200 | 20° C.-50° C. | [d] | [e] | Group (1) | no | 1:20-1:10,000 | [g] |
| 0.1-100 | 0° C.-250° C. | [d] | [e] | Group (1) | yes | 1:20-1:10,000 | [g] |
| 0.1-100 | 0° C.-250° C. | [d] | [e] | Group (1) | no | 1:20-1:10,000 | [g] |
| 0.1-100 | 0° C.-120° C. | [d] | [e] | Group (1) | yes | 1:20-1:10,000 | [g] |
| 0.1-100 | 0° C.-120° C. | [d] | [e] | Group (1) | no | 1:20-1:10,000 | [g] |
| 0.1-100 | 10° C.-100° C. | [d] | [e] | Group (1) | yes | 1:20-1:10,000 | [g] |
| 0.1-100 | 10° C.-100° C. | [d] | [e] | Group (1) | no | 1:20-1:10,000 | [g] |
| 0.1-100 | 20° C.-50° C. | [d] | [e] | Group (1) | yes | 1:20-1:10,000 | [g] |
| 0.1-100 | 20° C.-50° C. | [d] | [e] | Group (1) | no | 1:20-1:10,000 | [g] |
| 0.1-60 | 0° C.-250° C. | [d] | [e] | Group (1) | yes | 1:20-1:10,000 | [g] |
| 0.1-60 | 0° C.-250° C. | [d] | [e] | Group (1) | no | 1:20-1:10,000 | [g] |
| 0.1-60 | 0° C.-120° C. | [d] | [e] | Group (1) | yes | 1:20-1:10,000 | [g] |
| 0.1-60 | 0° C.-120° C. | [d] | [e] | Group (1) | no | 1:20-1:10,000 | [g] |
| 0.1-60 | 10° C.-100° C. | [d] | [e] | Group (1) | yes | 1:20-1:10,000 | [g] |
| 0.1-60 | 10° C.-100° C. | [d] | [e] | Group (1) | no | 1:20-1:10,000 | [g] |
| 0.1-60 | 20° C.-50° C. | [d] | [e] | Group (1) | yes | 1:20-1:10,000 | [g] |
| 0.1-60 | 20° C.-50° C. | [d] | [e] | Group (1) | no | 1:20-1:10,000 | [g] |
| 0.1-200 | 0° C.-250° C. | [d] | [e] | Group (2) | yes | 1:20-1:10,000 | [g] |
| 0.1-200 | 0° C.-250° C. | [d] | [e] | Group (2) | no | 1:20-1:10,000 | [g] |
| 0.1-200 | 0° C.-120° C. | [d] | [e] | Group (2) | yes | 1:20-1:10,000 | [g] |
| 0.1-200 | 0° C.-120° C. | [d] | [e] | Group (2) | no | 1:20-1:10,000 | [g] |
| 0.1-200 | 10° C.-100° C. | [d] | [e] | Group (2) | yes | 1:20-1:10,000 | [g] |
| 0.1-200 | 10° C.-100° C. | [d] | [e] | Group (2) | no | 1:20-1:10,000 | [g] |
| 0.1-200 | 20° C.-50° C. | [d] | [e] | Group (2) | yes | 1:20-1:10,000 | [g] |
| 0.1-200 | 20° C.-50° C. | [d] | [e] | Group (2) | no | 1:20-1:10,000 | [g] |
| 0.1-100 | 0° C.-250° C. | [d] | [e] | Group (2) | yes | 1:20-1:10,000 | [g] |
| 0.1-100 | 0° C.-250° C. | [d] | [e] | Group (2) | no | 1:20-1:10,000 | [g] |
| 0.1-100 | 0° C.-120° C. | [d] | [e] | Group (2) | yes | 1:20-1:10,000 | [g] |
| 0.1-100 | 0° C.-120° C. | [d] | [e] | Group (2) | no | 1:20-1:10,000 | [g] |
| 0.1-100 | 10° C.-100° C. | [d] | [e] | Group (2) | yes | 1:20-1:10,000 | [g] |
| 0.1-100 | 10° C.-100° C. | [d] | [e] | Group (2) | no | 1:20-1:10,000 | [g] |
| 0.1-100 | 20° C.-50° C. | [d] | [e] | Group (2) | yes | 1:20-1:10,000 | [g] |
| 0.1-100 | 20° C.-50° C. | [d] | [e] | Group (2) | no | 1:20-1:10,000 | [g] |
| 0.1-60 | 0° C.-250° C. | [d] | [e] | Group (2) | yes | 1:20-1:10,000 | [g] |

TABLE 3-continued

Preferred reaction conditions during the hydrogenation.

| Pressure [bar] | Temperatur [° C.] | Hydrogenation catalyst | Alkylating agent, molar ratio carbonyl: alkylating agent 1:1-1:2 | Base | Solvent | Molar ratio catalyst: starting material | Starting material |
|---|---|---|---|---|---|---|---|
| 0.1-60 | 0° C.-250° C. | [d] | [e] | Group (2) | no | 1:20-1:10,000 | [g] |
| 0.1-60 | 0° C.-120° C. | [d] | [e] | Group (2) | yes | 1:20-1:10,000 | [g] |
| 0.1-60 | 0° C.-120° C. | [d] | [e] | Group (2) | no | 1:20-1:10,000 | [g] |
| 0.1-60 | 10° C.-100° C. | [d] | [e] | Group (2) | yes | 1:20-1:10,000 | [g] |
| 0.1-60 | 10° C.-100° C. | [d] | [e] | Group (2) | no | 1:20-1:10,000 | [g] |
| 0.1-60 | 20° C.-50° C. | [d] | [e] | Group (2) | yes | 1:20-1:10,000 | [g] |
| 0.1-60 | 20° C.-50° C. | [d] | [e] | Group (2) | no | 1:20-1:10,000 | [g] |
| 0.1-200 | 0° C.-250° C. | [d] | [f] | Group (1) | yes | 1:20-1:10,000 | [g] |
| 0.1-200 | 0° C.-250° C. | [d] | [f] | Group (1) | no | 1:20-1:10,000 | [g] |
| 0.1-200 | 0° C.-120° C. | [d] | [f] | Group (1) | yes | 1:20-1:10,000 | [g] |
| 0.1-200 | 0° C.-120° C. | [d] | [f] | Group (1) | no | 1:20-1:10,000 | [g] |
| 0.1-200 | 10° C.-100° C. | [d] | [f] | Group (1) | yes | 1:20-1:10,000 | [g] |
| 0.1-200 | 10° C.-100° C. | [d] | [f] | Group (1) | no | 1:20-1:10,000 | [g] |
| 0.1-200 | 20° C.-50° C. | [d] | [f] | Group (1) | yes | 1:20-1:10,000 | [g] |
| 0.1-200 | 20° C.-50° C. | [d] | [f] | Group (1) | no | 1:20-1:10,000 | [g] |
| 0.1-100 | 0° C.-250° C. | [d] | [f] | Group (1) | yes | 1:20-1:10,000 | [g] |
| 0.1-100 | 0° C.-250° C. | [d] | [f] | Group (1) | no | 1:20-1:10,000 | [g] |
| 0.1-100 | 0° C.-120° C. | [d] | [f] | Group (1) | yes | 1:20-1:10,000 | [g] |
| 0.1-100 | 0° C.-120° C. | [d] | [f] | Group (1) | no | 1:20-1:10,000 | [g] |
| 0.1-100 | 10° C.-100° C. | [d] | [f] | Group (1) | yes | 1:20-1:10,000 | [g] |
| 0.1-100 | 10° C.-100° C. | [d] | [f] | Group (1) | no | 1:20-1:10,000 | [g] |
| 0.1-100 | 20° C.-50° C. | [d] | [f] | Group (1) | yes | 1:20-1:10,000 | [g] |
| 0.1-100 | 20° C.-50° C. | [d] | [f] | Group (1) | no | 1:20-1:10,000 | [g] |
| 0.1-60 | 0° C.-250° C. | [d] | [f] | Group (1) | yes | 1:20-1:10,000 | [g] |
| 0.1-60 | 0° C.-250° C. | [d] | [f] | Group (1) | no | 1:20-1:10,000 | [g] |
| 0.1-60 | 0° C.-120° C. | [d] | [f] | Group (1) | yes | 1:20-1:10,000 | [g] |
| 0.1-60 | 0° C.-120° C. | [d] | [f] | Group (1) | no | 1:20-1:10,000 | [g] |
| 0.1-60 | 10° C.-100° C. | [d] | [f] | Group (1) | yes | 1:20-1:10,000 | [g] |
| 0.1-60 | 10° C.-100° C. | [d] | [f] | Group (1) | no | 1:20-1:10,000 | [g] |
| 0.1-60 | 20° C.-50° C. | [d] | [f] | Group (1) | yes | 1:20-1:10,000 | [g] |
| 0.1-60 | 20° C.-50° C. | [d] | [f] | Group (1) | no | 1:20-1:10,000 | [g] |
| 0.1-200 | 0° C.-250° C. | [d] | [f] | Group (2) | yes | 1:20-1:10,000 | [g] |
| 0.1-200 | 0° C.-250° C. | [d] | [f] | Group (2) | no | 1:20-1:10,000 | [g] |
| 0.1-200 | 0° C.-120° C. | [d] | [f] | Group (2) | yes | 1:20-1:10,000 | [g] |
| 0.1-200 | 0° C.-120° C. | [d] | [f] | Group (2) | no | 1:20-1:10,000 | [g] |
| 0.1-200 | 10° C.-100° C. | [d] | [f] | Group (2) | yes | 1:20-1:10,000 | [g] |
| 0.1-200 | 10° C.-100° C. | [d] | [f] | Group (2) | no | 1:20-1:10,000 | [g] |
| 0.1-200 | 20° C.-50° C. | [d] | [f] | Group (2) | yes | 1:20-1:10,000 | [g] |
| 0.1-200 | 20° C.-50° C. | [d] | [f] | Group (2) | no | 1:20-1:10,000 | [g] |
| 0.1-100 | 0° C.-250° C. | [d] | [f] | Group (2) | yes | 1:20-1:10,000 | [g] |
| 0.1-100 | 0° C.-250° C. | [d] | [f] | Group (2) | no | 1:20-1:10,000 | [g] |
| 0.1-100 | 0° C.-120° C. | [d] | [f] | Group (2) | yes | 1:20-1:10,000 | [g] |
| 0.1-100 | 0° C.-120° C. | [d] | [f] | Group (2) | no | 1:20-1:10,000 | [g] |
| 0.1-100 | 10° C.-100° C. | [d] | [f] | Group (2) | yes | 1:20-1:10,000 | [g] |
| 0.1-100 | 10° C.-100° C. | [d] | [f] | Group (2) | no | 1:20-1:10,000 | [g] |
| 0.1-100 | 20° C.-50° C. | [d] | [f] | Group (2) | yes | 1:20-1:10,000 | [g] |
| 0.1-100 | 20° C.-50° C. | [d] | [f] | Group (2) | no | 1:20-1:10,000 | [g] |
| 0.1-60 | 0° C.-250° C. | [d] | [f] | Group (2) | yes | 1:20-1:10,000 | [g] |
| 0.1-60 | 0° C.-250° C. | [d] | [f] | Group (2) | no | 1:20-1:10,000 | [g] |
| 0.1-60 | 0° C.-120° C. | [d] | [f] | Group (2) | yes | 1:20-1:10,000 | [g] |
| 0.1-60 | 0° C.-120° C. | [d] | [f] | Group (2) | no | 1:20-1:10,000 | [g] |
| 0.1-60 | 10° C.-100° C. | [d] | [f] | Group (2) | yes | 1:20-1:10,000 | [g] |
| 0.1-60 | 10° C.-100° C. | [d] | [f] | Group (2) | no | 1:20-1:10,000 | [g] |
| 0.1-60 | 20° C.-50° C. | [d] | [f] | Group (2) | yes | 1:20-1:10,000 | [g] |
| 0.1-60 | 20° C.-50° C. | [d] | [f] | Group (2) | no | 1:20-1:10,000 | [g] |
| 0.1-200 | 0° C.-250° C. | [d] | [e] | Group (1) | yes | 1:20-1:10,000 | [h] |
| 0.1-200 | 0° C.-250° C. | [d] | [e] | Group (1) | no | 1:20-1:10,000 | [h] |
| 0.1-200 | 0° C.-120° C. | [d] | [e] | Group (1) | yes | 1:20-1:10,000 | [h] |
| 0.1-200 | 0° C.-120° C. | [d] | [e] | Group (1) | no | 1:20-1:10,000 | [h] |
| 0.1-200 | 10° C.-100° C. | [d] | [e] | Group (1) | yes | 1:20-1:10,000 | [h] |
| 0.1-200 | 10° C.-100° C. | [d] | [e] | Group (1) | no | 1:20-1:10,000 | [h] |
| 0.1-200 | 20° C.-50° C. | [d] | [e] | Group (1) | yes | 1:20-1:10,000 | [h] |
| 0.1-200 | 20° C.-50° C. | [d] | [e] | Group (1) | no | 1:20-1:10,000 | [h] |
| 0.1-100 | 0° C.-250° C. | [d] | [e] | Group (1) | yes | 1:20-1:10,000 | [h] |
| 0.1-100 | 0° C.-250° C. | [d] | [e] | Group (1) | no | 1:20-1:10,000 | [h] |
| 0.1-100 | 0° C.-120° C. | [d] | [e] | Group (1) | yes | 1:20-1:10,000 | [h] |
| 0.1-100 | 0° C.-120° C. | [d] | [e] | Group (1) | no | 1:20-1:10,000 | [h] |
| 0.1-100 | 10° C.-100° C. | [d] | [e] | Group (1) | yes | 1:20-1:10,000 | [h] |
| 0.1-100 | 10° C.-100° C. | [d] | [e] | Group (1) | no | 1:20-1:10,000 | [h] |
| 0.1-100 | 20° C.-50° C. | [d] | [e] | Group (1) | yes | 1:20-1:10,000 | [h] |
| 0.1-100 | 20° C.-50° C. | [d] | [e] | Group (1) | no | 1:20-1:10,000 | [h] |
| 0.1-60 | 0° C.-250° C. | [d] | [e] | Group (1) | yes | 1:20-1:10,000 | [h] |

TABLE 3-continued

Preferred reaction conditions during the hydrogenation.

| Pressure [bar] | Temperatur [° C.] | Hydrogenation catalyst | Alkylating agent, molar ratio carbonyl: alkylating agent 1:1-1:2 | Base | Solvent | Molar ratio catalyst: starting material | Starting material |
|---|---|---|---|---|---|---|---|
| 0.1-60 | 0° C.-250° C. | [d] | [e] | Group (1) | no | 1:20-1:10,000 | [h] |
| 0.1-60 | 0° C.-120° C. | [d] | [e] | Group (1) | yes | 1:20-1:10,000 | [h] |
| 0.1-60 | 0° C.-120° C. | [d] | [e] | Group (1) | no | 1:20-1:10,000 | [h] |
| 0.1-60 | 10° C.-100° C. | [d] | [e] | Group (1) | yes | 1:20-1:10,000 | [h] |
| 0.1-60 | 10° C.-100° C. | [d] | [e] | Group (1) | no | 1:20-1:10,000 | [h] |
| 0.1-60 | 20° C.-50° C. | [d] | [e] | Group (1) | yes | 1:20-1:10,000 | [h] |
| 0.1-60 | 20° C.-50° C. | [d] | [e] | Group (1) | no | 1:20-1:10,000 | [h] |
| 0.1-200 | 0° C.-250° C. | [d] | [e] | Group (2) | yes | 1:20-1:10,000 | [h] |
| 0.1-200 | 0° C.-250° C. | [d] | [e] | Group (2) | no | 1:20-1:10,000 | [h] |
| 0.1-200 | 0° C.-120° C. | [d] | [e] | Group (2) | yes | 1:20-1:10,000 | [h] |
| 0.1-200 | 0° C.-120° C. | [d] | [e] | Group (2) | no | 1:20-1:10,000 | [h] |
| 0.1-200 | 10° C.-100° C. | [d] | [e] | Group (2) | yes | 1:20-1:10,000 | [h] |
| 0.1-200 | 10° C.-100° C. | [d] | [e] | Group (2) | no | 1:20-1:10,000 | [h] |
| 0.1-200 | 20° C.-50° C. | [d] | [e] | Group (2) | yes | 1:20-1:10,000 | [h] |
| 0.1-200 | 20° C.-50° C. | [d] | [e] | Group (2) | no | 1:20-1:10,000 | [h] |
| 0.1-100 | 0° C.-250° C. | [d] | [e] | Group (2) | yes | 1:20-1:10,000 | [h] |
| 0.1-100 | 0° C.-250° C. | [d] | [e] | Group (2) | no | 1:20-1:10,000 | [h] |
| 0.1-100 | 0° C.-120° C. | [d] | [e] | Group (2) | yes | 1:20-1:10,000 | [h] |
| 0.1-100 | 0° C.-120° C. | [d] | [e] | Group (2) | no | 1:20-1:10,000 | [h] |
| 0.1-100 | 10° C.-100° C. | [d] | [e] | Group (2) | yes | 1:20-1:10,000 | [h] |
| 0.1-100 | 10° C.-100° C. | [d] | [e] | Group (2) | no | 1:20-1:10,000 | [h] |
| 0.1-100 | 20° C.-50° C. | [d] | [e] | Group (2) | yes | 1:20-1:10,000 | [h] |
| 0.1-100 | 20° C.-50° C. | [d] | [e] | Group (2) | no | 1:20-1:10,000 | [h] |
| 0.1-60 | 0° C.-250° C. | [d] | [e] | Group (2) | yes | 1:20-1:10,000 | [h] |
| 0.1-60 | 0° C.-250° C. | [d] | [e] | Group (2) | no | 1:20-1:10,000 | [h] |
| 0.1-60 | 0° C.-120° C. | [d] | [e] | Group (2) | yes | 1:20-1:10,000 | [h] |
| 0.1-60 | 0° C.-120° C. | [d] | [e] | Group (2) | no | 1:20-1:10,000 | [h] |
| 0.1-60 | 10° C.-100° C. | [d] | [e] | Group (2) | yes | 1:20-1:10,000 | [h] |
| 0.1-60 | 10° C.-100° C. | [d] | [e] | Group (2) | no | 1:20-1:10,000 | [h] |
| 0.1-60 | 20° C.-50° C. | [d] | [e] | Group (2) | yes | 1:20-1:10,000 | [h] |
| 0.1-60 | 20° C.-50° C. | [d] | [e] | Group (2) | no | 1:20-1:10,000 | [h] |
| 0.1-200 | 0° C.-250° C. | [d] | [f] | Group (1) | yes | 1:20-1:10,000 | [h] |
| 0.1-200 | 0° C.-250° C. | [d] | [f] | Group (1) | no | 1:20-1:10,000 | [h] |
| 0.1-200 | 0° C.-120° C. | [d] | [f] | Group (1) | yes | 1:20-1:10,000 | [h] |
| 0.1-200 | 0° C.-120° C. | [d] | [f] | Group (1) | no | 1:20-1:10,000 | [h] |
| 0.1-200 | 10° C.-100° C. | [d] | [f] | Group (1) | yes | 1:20-1:10,000 | [h] |
| 0.1-200 | 10° C.-100° C. | [d] | [f] | Group (1) | no | 1:20-1:10,000 | [h] |
| 0.1-200 | 20° C.-50° C. | [d] | [f] | Group (1) | yes | 1:20-1:10,000 | [h] |
| 0.1-200 | 20° C.-50° C. | [d] | [f] | Group (1) | no | 1:20-1:10,000 | [h] |
| 0.1-100 | 0° C.-250° C. | [d] | [f] | Group (1) | yes | 1:20-1:10,000 | [h] |
| 0.1-100 | 0° C.-250° C. | [d] | [f] | Group (1) | no | 1:20-1:10,000 | [h] |
| 0.1-100 | 0° C.-120° C. | [d] | [f] | Group (1) | yes | 1:20-1:10,000 | [h] |
| 0.1-100 | 0° C.-120° C. | [d] | [f] | Group (1) | no | 1:20-1:10,000 | [h] |
| 0.1-100 | 10° C.-100° C. | [d] | [f] | Group (1) | yes | 1:20-1:10,000 | [h] |
| 0.1-100 | 10° C.-100° C. | [d] | [f] | Group (1) | no | 1:20-1:10,000 | [h] |
| 0.1-100 | 20° C.-50° C. | [d] | [f] | Group (1) | yes | 1:20-1:10,000 | [h] |
| 0.1-100 | 20° C.-50° C. | [d] | [f] | Group (1) | no | 1:20-1:10,000 | [h] |
| 0.1-60 | 0° C.-250° C. | [d] | [f] | Group (1) | yes | 1:20-1:10,000 | [h] |
| 0.1-60 | 0° C.-250° C. | [d] | [f] | Group (1) | no | 1:20-1:10,000 | [h] |
| 0.1-60 | 0° C.-120° C. | [d] | [f] | Group (1) | yes | 1:20-1:10,000 | [h] |
| 0.1-60 | 0° C.-120° C. | [d] | [f] | Group (1) | no | 1:20-1:10,000 | [h] |
| 0.1-60 | 10° C.-100° C. | [d] | [f] | Group (1) | yes | 1:20-1:10,000 | [h] |
| 0.1-60 | 10° C.-100° C. | [d] | [f] | Group (1) | no | 1:20-1:10,000 | [h] |
| 0.1-60 | 20° C.-50° C. | [d] | [f] | Group (1) | yes | 1:20-1:10,000 | [h] |
| 0.1-60 | 20° C.-50° C. | [d] | [f] | Group (1) | no | 1:20-1:10,000 | [h] |
| 0.1-200 | 0° C.-250° C. | [d] | [f] | Group (2) | yes | 1:20-1:10,000 | [h] |
| 0.1-200 | 0° C.-250° C. | [d] | [f] | Group (2) | no | 1:20-1:10,000 | [h] |
| 0.1-200 | 0° C.-120° C. | [d] | [f] | Group (2) | yes | 1:20-1:10,000 | [h] |
| 0.1-200 | 0° C.-120° C. | [d] | [f] | Group (2) | no | 1:20-1:10,000 | [h] |
| 0.1-200 | 10° C.-100° C. | [d] | [f] | Group (2) | yes | 1:20-1:10,000 | [h] |
| 0.1-200 | 10° C.-100° C. | [d] | [f] | Group (2) | no | 1:20-1:10,000 | [h] |
| 0.1-200 | 20° C.-50° C. | [d] | [f] | Group (2) | yes | 1:20-1:10,000 | [h] |
| 0.1-200 | 20° C.-50° C. | [d] | [f] | Group (2) | no | 1:20-1:10,000 | [h] |
| 0.1-100 | 0° C.-250° C. | [d] | [f] | Group (2) | yes | 1:20-1:10,000 | [h] |
| 0.1-100 | 0° C.-250° C. | [d] | [f] | Group (2) | no | 1:20-1:10,000 | [h] |
| 0.1-100 | 0° C.-120° C. | [d] | [f] | Group (2) | yes | 1:20-1:10,000 | [h] |
| 0.1-100 | 0° C.-120° C. | [d] | [f] | Group (2) | no | 1:20-1:10,000 | [h] |
| 0.1-100 | 10° C.-100° C. | [d] | [f] | Group (2) | yes | 1:20-1:10,000 | [h] |
| 0.1-100 | 10° C.-100° C. | [d] | [f] | Group (2) | no | 1:20-1:10,000 | [h] |
| 0.1-100 | 20° C.-50° C. | [d] | [f] | Group (2) | yes | 1:20-1:10,000 | [h] |
| 0.1-100 | 20° C.-50° C. | [d] | [f] | Group (2) | no | 1:20-1:10,000 | [h] |
| 0.1-60 | 0° C.-250° C. | [d] | [f] | Group (2) | yes | 1:20-1:10,000 | [h] |

TABLE 3-continued

Preferred reaction conditions during the hydrogenation.

| Pressure [bar] | Temperatur [° C.] | Hydrogenation catalyst | Alkylating agent, molar ratio carbonyl: alkylating agent 1:1-1:2 | Base | Solvent | Molar ratio catalyst: starting material | Starting material |
|---|---|---|---|---|---|---|---|
| 0.1-60 | 0° C.-250° C. | [d] | [f] | Group (2) | no | 1:20-1:10,000 | [h] |
| 0.1-60 | 0° C.-120° C. | [d] | [f] | Group (2) | yes | 1:20-1:10,000 | [h] |
| 0.1-60 | 0° C.-120° C. | [d] | [f] | Group (2) | no | 1:20-1:10,000 | [h] |
| 0.1-60 | 10° C.-100° C. | [d] | [f] | Group (2) | yes | 1:20-1:10,000 | [h] |
| 0.1-60 | 10° C.-100° C. | [d] | [f] | Group (2) | no | 1:20-1:10,000 | [h] |
| 0.1-60 | 20° C.-50° C. | [d] | [f] | Group (2) | yes | 1:20-1:10,000 | [h] |
| 0.1-60 | 20° C.-50° C. | [d] | [f] | Group (2) | no | 1:20-1:10,000 | [h] |
| 0.1-200 | 0° C.-250° C. | [d] | [e] | Group (1) | yes | 1:20-1:10,000 | [i] |
| 0.1-200 | 0° C.-250° C. | [d] | [e] | Group (1) | no | 1:20-1:10,000 | [i] |
| 0.1-200 | 0° C.-120° C. | [d] | [e] | Group (1) | yes | 1:20-1:10,000 | [i] |
| 0.1-200 | 0° C.-120° C. | [d] | [e] | Group (1) | no | 1:20-1:10,000 | [i] |
| 0.1-200 | 10° C.-100° C. | [d] | [e] | Group (1) | yes | 1:20-1:10,000 | [i] |
| 0.1-200 | 10° C.-100° C. | [d] | [e] | Group (1) | no | 1:20-1:10,000 | [i] |
| 0.1-200 | 20° C.-50° C. | [d] | [e] | Group (1) | yes | 1:20-1:10,000 | [i] |
| 0.1-200 | 20° C.-50° C. | [d] | [e] | Group (1) | no | 1:20-1:10,000 | [i] |
| 0.1-100 | 0° C.-250° C. | [d] | [e] | Group (1) | yes | 1:20-1:10,000 | [i] |
| 0.1-100 | 0° C.-250° C. | [d] | [e] | Group (1) | no | 1:20-1:10,000 | [i] |
| 0.1-100 | 0° C.-120° C. | [d] | [e] | Group (1) | yes | 1:20-1:10,000 | [i] |
| 0.1-100 | 0° C.-120° C. | [d] | [e] | Group (1) | no | 1:20-1:10,000 | [i] |
| 0.1-100 | 10° C.-100° C. | [d] | [e] | Group (1) | yes | 1:20-1:10,000 | [i] |
| 0.1-100 | 10° C.-100° C. | [d] | [e] | Group (1) | no | 1:20-1:10,000 | [i] |
| 0.1-100 | 20° C.-50° C. | [d] | [e] | Group (1) | yes | 1:20-1:10,000 | [i] |
| 0.1-100 | 20° C.-50° C. | [d] | [e] | Group (1) | no | 1:20-1:10,000 | [i] |
| 0.1-60 | 0° C.-250° C. | [d] | [e] | Group (1) | yes | 1:20-1:10,000 | [i] |
| 0.1-60 | 0° C.-250° C. | [d] | [e] | Group (1) | no | 1:20-1:10,000 | [i] |
| 0.1-60 | 0° C.-120° C. | [d] | [e] | Group (1) | yes | 1:20-1:10,000 | [i] |
| 0.1-60 | 0° C.-120° C. | [d] | [e] | Group (1) | no | 1:20-1:10,000 | [i] |
| 0.1-60 | 10° C.-100° C. | [d] | [e] | Group (1) | yes | 1:20-1:10,000 | [i] |
| 0.1-60 | 10° C.-100° C. | [d] | [e] | Group (1) | no | 1:20-1:10,000 | [i] |
| 0.1-60 | 20° C.-50° C. | [d] | [e] | Group (1) | yes | 1:20-1:10,000 | [i] |
| 0.1-60 | 20° C.-50° C. | [d] | [e] | Group (1) | no | 1:20-1:10,000 | [i] |
| 0.1-200 | 0° C.-250° C. | [d] | [e] | Group (2) | yes | 1:20-1:10,000 | [i] |
| 0.1-200 | 0° C.-250° C. | [d] | [e] | Group (2) | no | 1:20-1:10,000 | [i] |
| 0.1-200 | 0° C.-120° C. | [d] | [e] | Group (2) | yes | 1:20-1:10,000 | [i] |
| 0.1-200 | 0° C.-120° C. | [d] | [e] | Group (2) | no | 1:20-1:10,000 | [i] |
| 0.1-200 | 10° C.-100° C. | [d] | [e] | Group (2) | yes | 1:20-1:10,000 | [i] |
| 0.1-200 | 10° C.-100° C. | [d] | [e] | Group (2) | no | 1:20-1:10,000 | [i] |
| 0.1-200 | 20° C.-50° C. | [d] | [e] | Group (2) | yes | 1:20-1:10,000 | [i] |
| 0.1-200 | 20° C.-50° C. | [d] | [e] | Group (2) | no | 1:20-1:10,000 | [i] |
| 0.1-100 | 0° C.-250° C. | [d] | [e] | Group (2) | yes | 1:20-1:10,000 | [i] |
| 0.1-100 | 0° C.-250° C. | [d] | [e] | Group (2) | no | 1:20-1:10,000 | [i] |
| 0.1-100 | 0° C.-120° C. | [d] | [e] | Group (2) | yes | 1:20-1:10,000 | [i] |
| 0.1-100 | 0° C.-120° C. | [d] | [e] | Group (2) | no | 1:20-1:10,000 | [i] |
| 0.1-100 | 10° C.-100° C. | [d] | [e] | Group (2) | yes | 1:20-1:10,000 | [i] |
| 0.1-100 | 10° C.-100° C. | [d] | [e] | Group (2) | no | 1:20-1:10,000 | [i] |
| 0.1-100 | 20° C.-50° C. | [d] | [e] | Group (2) | yes | 1:20-1:10,000 | [i] |
| 0.1-100 | 20° C.-50° C. | [d] | [e] | Group (2) | no | 1:20-1:10,000 | [i] |
| 0.1-60 | 0° C.-250° C. | [d] | [e] | Group (2) | yes | 1:20-1:10,000 | [i] |
| 0.1-60 | 0° C.-250° C. | [d] | [e] | Group (2) | no | 1:20-1:10,000 | [i] |
| 0.1-60 | 0° C.-120° C. | [d] | [e] | Group (2) | yes | 1:20-1:10,000 | [i] |
| 0.1-60 | 0° C.-120° C. | [d] | [e] | Group (2) | no | 1:20-1:10,000 | [i] |
| 0.1-60 | 10° C.-100° C. | [d] | [e] | Group (2) | yes | 1:20-1:10,000 | [i] |
| 0.1-60 | 10° C.-100° C. | [d] | [e] | Group (2) | no | 1:20-1:10,000 | [i] |
| 0.1-60 | 20° C.-50° C. | [d] | [e] | Group (2) | yes | 1:20-1:10,000 | [i] |
| 0.1-60 | 20° C.-50° C. | [d] | [e] | Group (2) | no | 1:20-1:10,000 | [i] |
| 0.1-200 | 0° C.-250° C. | [d] | [f] | Group (1) | yes | 1:20-1:10,000 | [i] |
| 0.1-200 | 0° C.-250° C. | [d] | [f] | Group (1) | no | 1:20-1:10,000 | [i] |
| 0.1-200 | 0° C.-120° C. | [d] | [f] | Group (1) | yes | 1:20-1:10,000 | [i] |
| 0.1-200 | 0° C.-120° C. | [d] | [f] | Group (1) | no | 1:20-1:10,000 | [i] |
| 0.1-200 | 10° C.-100° C. | [d] | [f] | Group (1) | yes | 1:20-1:10,000 | [i] |
| 0.1-200 | 10° C.-100° C. | [d] | [f] | Group (1) | no | 1:20-1:10,000 | [i] |
| 0.1-200 | 20° C.-50° C. | [d] | [f] | Group (1) | yes | 1:20-1:10,000 | [i] |
| 0.1-200 | 20° C.-50° C. | [d] | [f] | Group (1) | no | 1:20-1:10,000 | [i] |
| 0.1-100 | 0° C.-250° C. | [d] | [f] | Group (1) | yes | 1:20-1:10,000 | [i] |
| 0.1-100 | 0° C.-250° C. | [d] | [f] | Group (1) | no | 1:20-1:10,000 | [i] |
| 0.1-100 | 0° C.-120° C. | [d] | [f] | Group (1) | yes | 1:20-1:10,000 | [i] |
| 0.1-100 | 0° C.-120° C. | [d] | [f] | Group (1) | no | 1:20-1:10,000 | [i] |
| 0.1-100 | 10° C.-100° C. | [d] | [f] | Group (1) | yes | 1:20-1:10,000 | [i] |
| 0.1-100 | 10° C.-100° C. | [d] | [f] | Group (1) | no | 1:20-1:10,000 | [i] |
| 0.1-100 | 20° C.-50° C. | [d] | [f] | Group (1) | yes | 1:20-1:10,000 | [i] |
| 0.1-100 | 20° C.-50° C. | [d] | [f] | Group (1) | no | 1:20-1:10,000 | [i] |
| 0.1-60 | 0° C.-250° C. | [d] | [f] | Group (1) | yes | 1:20-1:10,000 | [i] |

TABLE 3-continued

Preferred reaction conditions during the hydrogenation.

| Pressure [bar] | Temperatur [° C.] | Hydrogenation catalyst | Alkylating agent, molar ratio carbonyl: alkylating agent 1:1-1:2 | Base | Solvent | Molar ratio catalyst: starting material | Starting material |
|---|---|---|---|---|---|---|---|
| 0.1-60  | 0° C.-250° C. | [d] | [f] | Group (1) | no  | 1:20-1:10,000 | [i] |
| 0.1-60  | 0° C.-120° C. | [d] | [f] | Group (1) | yes | 1:20-1:10,000 | [i] |
| 0.1-60  | 0° C.-120° C. | [d] | [f] | Group (1) | no  | 1:20-1:10,000 | [i] |
| 0.1-60  | 10° C.-100° C.| [d] | [f] | Group (1) | yes | 1:20-1:10,000 | [i] |
| 0.1-60  | 10° C.-100° C.| [d] | [f] | Group (1) | no  | 1:20-1:10,000 | [i] |
| 0.1-60  | 20° C.-50° C. | [d] | [f] | Group (1) | yes | 1:20-1:10,000 | [i] |
| 0.1-60  | 20° C.-50° C. | [d] | [f] | Group (1) | no  | 1:20-1:10,000 | [i] |
| 0.1-200 | 0° C.-250° C. | [d] | [f] | Group (2) | yes | 1:20-1:10,000 | [i] |
| 0.1-200 | 0° C.-250° C. | [d] | [f] | Group (2) | no  | 1:20-1:10,000 | [i] |
| 0.1-200 | 0° C.-120° C. | [d] | [f] | Group (2) | yes | 1:20-1:10,000 | [i] |
| 0.1-200 | 0° C.-120° C. | [d] | [f] | Group (2) | no  | 1:20-1:10,000 | [i] |
| 0.1-200 | 10° C.-100° C.| [d] | [f] | Group (2) | yes | 1:20-1:10,000 | [i] |
| 0.1-200 | 10° C.-100° C.| [d] | [f] | Group (2) | no  | 1:20-1:10,000 | [i] |
| 0.1-200 | 20° C.-50° C. | [d] | [f] | Group (2) | yes | 1:20-1:10,000 | [i] |
| 0.1-200 | 20° C.-50° C. | [d] | [f] | Group (2) | no  | 1:20-1:10,000 | [i] |
| 0.1-100 | 0° C.-250° C. | [d] | [f] | Group (2) | yes | 1:20-1:10,000 | [i] |
| 0.1-100 | 0° C.-250° C. | [d] | [f] | Group (2) | no  | 1:20-1:10,000 | [i] |
| 0.1-100 | 0° C.-120° C. | [d] | [f] | Group (2) | yes | 1:20-1:10,000 | [i] |
| 0.1-100 | 0° C.-120° C. | [d] | [f] | Group (2) | no  | 1:20-1:10,000 | [i] |
| 0.1-100 | 10° C.-100° C.| [d] | [f] | Group (2) | yes | 1:20-1:10,000 | [i] |
| 0.1-100 | 10° C.-100° C.| [d] | [f] | Group (2) | no  | 1:20-1:10,000 | [i] |
| 0.1-100 | 20° C.-50° C. | [d] | [f] | Group (2) | yes | 1:20-1:10,000 | [i] |
| 0.1-100 | 20° C.-50° C. | [d] | [f] | Group (2) | no  | 1:20-1:10,000 | [i] |
| 0.1-60  | 0° C.-250° C. | [d] | [f] | Group (2) | yes | 1:20-1:10,000 | [i] |
| 0.1-60  | 0° C.-250° C. | [d] | [f] | Group (2) | no  | 1:20-1:10,000 | [i] |
| 0.1-60  | 0° C.-120° C. | [d] | [f] | Group (2) | yes | 1:20-1:10,000 | [i] |
| 0.1-60  | 0° C.-120° C. | [d] | [f] | Group (2) | no  | 1:20-1:10,000 | [i] |
| 0.1-60  | 10° C.-100° C.| [d] | [f] | Group (2) | yes | 1:20-1:10,000 | [i] |
| 0.1-60  | 10° C.-100° C.| [d] | [f] | Group (2) | no  | 1:20-1:10,000 | [i] |
| 0.1-60  | 20° C.-50° C. | [d] | [f] | Group (2) | yes | 1:20-1:10,000 | [i] |
| 0.1-60  | 20° C.-50° C. | [d] | [f] | Group (2) | no  | 1:20-1:10,000 | [i] |
| 0.1-200 | 0° C.-250° C. | [b] | [e] | Group (1) | yes | 1:50-1:2,000 | [g] |
| 0.1-200 | 0° C.-250° C. | [b] | [e] | Group (1) | no  | 1:50-1:2,000 | [g] |
| 0.1-200 | 0° C.-120° C. | [b] | [e] | Group (1) | yes | 1:50-1:2,000 | [g] |
| 0.1-200 | 0° C.-120° C. | [b] | [e] | Group (1) | no  | 1:50-1:2,000 | [g] |
| 0.1-200 | 10° C.-100° C.| [b] | [e] | Group (1) | yes | 1:50-1:2,000 | [g] |
| 0.1-200 | 10° C.-100° C.| [b] | [e] | Group (1) | no  | 1:50-1:2,000 | [g] |
| 0.1-200 | 20° C.-50° C. | [b] | [e] | Group (1) | yes | 1:50-1:2,000 | [g] |
| 0.1-200 | 20° C.-50° C. | [b] | [e] | Group (1) | no  | 1:50-1:2,000 | [g] |
| 0.1-100 | 0° C.-250° C. | [b] | [e] | Group (1) | yes | 1:50-1:2,000 | [g] |
| 0.1-100 | 0° C.-250° C. | [b] | [e] | Group (1) | no  | 1:50-1:2,000 | [g] |
| 0.1-100 | 0° C.-120° C. | [b] | [e] | Group (1) | yes | 1:50-1:2,000 | [g] |
| 0.1-100 | 0° C.-120° C. | [b] | [e] | Group (1) | no  | 1:50-1:2,000 | [g] |
| 0.1-100 | 10° C.-100° C.| [b] | [e] | Group (1) | yes | 1:50-1:2,000 | [g] |
| 0.1-100 | 10° C.-100° C.| [b] | [e] | Group (1) | no  | 1:50-1:2,000 | [g] |
| 0.1-100 | 20° C.-50° C. | [b] | [e] | Group (1) | yes | 1:50-1:2,000 | [g] |
| 0.1-100 | 20° C.-50° C. | [b] | [e] | Group (1) | no  | 1:50-1:2,000 | [g] |
| 0.1-60  | 0° C.-250° C. | [b] | [e] | Group (1) | yes | 1:50-1:2,000 | [g] |
| 0.1-60  | 0° C.-250° C. | [b] | [e] | Group (1) | no  | 1:50-1:2,000 | [g] |
| 0.1-60  | 0° C.-120° C. | [b] | [e] | Group (1) | yes | 1:50-1:2,000 | [g] |
| 0.1-60  | 0° C.-120° C. | [b] | [e] | Group (1) | no  | 1:50-1:2,000 | [g] |
| 0.1-60  | 10° C.-100° C.| [b] | [e] | Group (1) | yes | 1:50-1:2,000 | [g] |
| 0.1-60  | 10° C.-100° C.| [b] | [e] | Group (1) | no  | 1:50-1:2,000 | [g] |
| 0.1-60  | 20° C.-50° C. | [b] | [e] | Group (1) | yes | 1:50-1:2,000 | [g] |
| 0.1-60  | 20° C.-50° C. | [b] | [e] | Group (1) | no  | 1:50-1:2,000 | [g] |
| 0.1-200 | 0° C.-250° C. | [b] | [e] | Group (2) | yes | 1:50-1:2,000 | [g] |
| 0.1-200 | 0° C.-250° C. | [b] | [e] | Group (2) | no  | 1:50-1:2,000 | [g] |
| 0.1-200 | 0° C.-120° C. | [b] | [e] | Group (2) | yes | 1:50-1:2,000 | [g] |
| 0.1-200 | 0° C.-120° C. | [b] | [e] | Group (2) | no  | 1:50-1:2,000 | [g] |
| 0.1-200 | 10° C.-100° C.| [b] | [e] | Group (2) | yes | 1:50-1:2,000 | [g] |
| 0.1-200 | 10° C.-100° C.| [b] | [e] | Group (2) | no  | 1:50-1:2,000 | [g] |
| 0.1-200 | 20° C.-50° C. | [b] | [e] | Group (2) | yes | 1:50-1:2,000 | [g] |
| 0.1-200 | 20° C.-50° C. | [b] | [e] | Group (2) | no  | 1:50-1:2,000 | [g] |
| 0.1-100 | 0° C.-250° C. | [b] | [e] | Group (2) | yes | 1:50-1:2,000 | [g] |
| 0.1-100 | 0° C.-250° C. | [b] | [e] | Group (2) | no  | 1:50-1:2,000 | [g] |
| 0.1-100 | 0° C.-120° C. | [b] | [e] | Group (2) | yes | 1:50-1:2,000 | [g] |
| 0.1-100 | 0° C.-120° C. | [b] | [e] | Group (2) | no  | 1:50-1:2,000 | [g] |
| 0.1-100 | 10° C.-100° C.| [b] | [e] | Group (2) | yes | 1:50-1:2,000 | [g] |
| 0.1-100 | 10° C.-100° C.| [b] | [e] | Group (2) | no  | 1:50-1:2,000 | [g] |
| 0.1-100 | 20° C.-50° C. | [b] | [e] | Group (2) | yes | 1:50-1:2,000 | [g] |
| 0.1-100 | 20° C.-50° C. | [b] | [e] | Group (2) | no  | 1:50-1:2,000 | [g] |
| 0.1-60  | 0° C.-250° C. | [b] | [e] | Group (2) | yes | 1:50-1:2,000 | [g] |

TABLE 3-continued

Preferred reaction conditions during the hydrogenation.

| Pressure [bar] | Temperatur [° C.] | Hydrogenation catalyst | Alkylating agent, molar ratio carbonyl: alkylating agent 1:1-1:2 | Base | Solvent | Molar ratio catalyst: starting material | Starting material |
|---|---|---|---|---|---|---|---|
| 0.1-60 | 0° C.-250° C. | [b] | [e] | Group (2) | no | 1:50-1:2,000 | [g] |
| 0.1-60 | 0° C.-120° C. | [b] | [e] | Group (2) | yes | 1:50-1:2,000 | [g] |
| 0.1-60 | 0° C.-120° C. | [b] | [e] | Group (2) | no | 1:50-1:2,000 | [g] |
| 0.1-60 | 10° C.-100° C. | [b] | [e] | Group (2) | yes | 1:50-1:2,000 | [g] |
| 0.1-60 | 10° C.-100° C. | [b] | [e] | Group (2) | no | 1:50-1:2,000 | [g] |
| 0.1-60 | 20° C.-50° C. | [b] | [e] | Group (2) | yes | 1:50-1:2,000 | [g] |
| 0.1-60 | 20° C.-50° C. | [b] | [e] | Group (2) | no | 1:50-1:2,000 | [g] |
| 0.1-200 | 0° C.-250° C. | [c] | [e] | Group (1) | yes | 1:50-1:2,000 | [g] |
| 0.1-200 | 0° C.-250° C. | [c] | [e] | Group (1) | no | 1:50-1:2,000 | [g] |
| 0.1-200 | 0° C.-120° C. | [c] | [e] | Group (1) | yes | 1:50-1:2,000 | [g] |
| 0.1-200 | 0° C.-120° C. | [c] | [e] | Group (1) | no | 1:50-1:2,000 | [g] |
| 0.1-200 | 10° C.-100° C. | [c] | [e] | Group (1) | yes | 1:50-1:2,000 | [g] |
| 0.1-200 | 10° C.-100° C. | [c] | [e] | Group (1) | no | 1:50-1:2,000 | [g] |
| 0.1-200 | 20° C.-50° C. | [c] | [e] | Group (1) | yes | 1:50-1:2,000 | [g] |
| 0.1-200 | 20° C.-50° C. | [c] | [e] | Group (1) | no | 1:50-1:2,000 | [g] |
| 0.1-100 | 0° C.-250° C. | [c] | [e] | Group (1) | yes | 1:50-1:2,000 | [g] |
| 0.1-100 | 0° C.-250° C. | [c] | [e] | Group (1) | no | 1:50-1:2,000 | [g] |
| 0.1-100 | 0° C.-120° C. | [c] | [e] | Group (1) | yes | 1:50-1:2,000 | [g] |
| 0.1-100 | 0° C.-120° C. | [c] | [e] | Group (1) | no | 1:50-1:2,000 | [g] |
| 0.1-100 | 10° C.-100° C. | [c] | [e] | Group (1) | yes | 1:50-1:2,000 | [g] |
| 0.1-100 | 10° C.-100° C. | [c] | [e] | Group (1) | no | 1:50-1:2,000 | [g] |
| 0.1-100 | 20° C.-50° C. | [c] | [e] | Group (1) | yes | 1:50-1:2,000 | [g] |
| 0.1-100 | 20° C.-50° C. | [c] | [e] | Group (1) | no | 1:50-1:2,000 | [g] |
| 0.1-60 | 0° C.-250° C. | [c] | [e] | Group (1) | yes | 1:50-1:2,000 | [g] |
| 0.1-60 | 0° C.-250° C. | [c] | [e] | Group (1) | no | 1:50-1:2,000 | [g] |
| 0.1-60 | 0° C.-120° C. | [c] | [e] | Group (1) | yes | 1:50-1:2,000 | [g] |
| 0.1-60 | 0° C.-120° C. | [c] | [e] | Group (1) | no | 1:50-1:2,000 | [g] |
| 0.1-60 | 10° C.-100° C. | [c] | [e] | Group (1) | yes | 1:50-1:2,000 | [g] |
| 0.1-60 | 10° C.-100° C. | [c] | [e] | Group (1) | no | 1:50-1:2,000 | [g] |
| 0.1-60 | 20° C.-50° C. | [c] | [e] | Group (1) | yes | 1:50-1:2,000 | [g] |
| 0.1-60 | 20° C.-50° C. | [c] | [e] | Group (1) | no | 1:50-1:2,000 | [g] |
| 0.1-200 | 0° C.-250° C. | [c] | [e] | Group (2) | yes | 1:50-1:2,000 | [g] |
| 0.1-200 | 0° C.-250° C. | [c] | [e] | Group (2) | no | 1:50-1:2,000 | [g] |
| 0.1-200 | 0° C.-120° C. | [c] | [e] | Group (2) | yes | 1:50-1:2,000 | [g] |
| 0.1-200 | 0° C.-120° C. | [c] | [e] | Group (2) | no | 1:50-1:2,000 | [g] |
| 0.1-200 | 10° C.-100° C. | [c] | [e] | Group (2) | yes | 1:50-1:2,000 | [g] |
| 0.1-200 | 10° C.-100° C. | [c] | [e] | Group (2) | no | 1:50-1:2,000 | [g] |
| 0.1-200 | 20° C.-50° C. | [c] | [e] | Group (2) | yes | 1:50-1:2,000 | [g] |
| 0.1-200 | 20° C.-50° C. | [c] | [e] | Group (2) | no | 1:50-1:2,000 | [g] |
| 0.1-100 | 0° C.-250° C. | [c] | [e] | Group (2) | yes | 1:50-1:2,000 | [g] |
| 0.1-100 | 0° C.-250° C. | [c] | [e] | Group (2) | no | 1:50-1:2,000 | [g] |
| 0.1-100 | 0° C.-120° C. | [c] | [e] | Group (2) | yes | 1:50-1:2,000 | [g] |
| 0.1-100 | 0° C.-120° C. | [c] | [e] | Group (2) | no | 1:50-1:2,000 | [g] |
| 0.1-100 | 10° C.-100° C. | [c] | [e] | Group (2) | yes | 1:50-1:2,000 | [g] |
| 0.1-100 | 10° C.-100° C. | [c] | [e] | Group (2) | no | 1:50-1:2,000 | [g] |
| 0.1-100 | 20° C.-50° C. | [c] | [e] | Group (2) | yes | 1:50-1:2,000 | [g] |
| 0.1-100 | 20° C.-50° C. | [c] | [e] | Group (2) | no | 1:50-1:2,000 | [g] |
| 0.1-60 | 0° C.-250° C. | [c] | [e] | Group (2) | yes | 1:50-1:2,000 | [g] |
| 0.1-60 | 0° C.-250° C. | [c] | [e] | Group (2) | no | 1:50-1:2,000 | [g] |
| 0.1-60 | 0° C.-120° C. | [c] | [e] | Group (2) | yes | 1:50-1:2,000 | [g] |
| 0.1-60 | 0° C.-120° C. | [c] | [e] | Group (2) | no | 1:50-1:2,000 | [g] |
| 0.1-60 | 10° C.-100° C. | [c] | [e] | Group (2) | yes | 1:50-1:2,000 | [g] |
| 0.1-60 | 10° C.-100° C. | [c] | [e] | Group (2) | no | 1:50-1:2,000 | [g] |
| 0.1-60 | 20° C.-50° C. | [c] | [e] | Group (2) | yes | 1:50-1:2,000 | [g] |
| 0.1-60 | 20° C.-50° C. | [c] | [e] | Group (2) | no | 1:50-1:2,000 | [g] |
| 0.1-200 | 0° C.-250° C. | [d] | [e] | Group (1) | yes | 1:50-1:2,000 | [g] |
| 0.1-200 | 0° C.-250° C. | [d] | [e] | Group (1) | no | 1:50-1:2,000 | [g] |
| 0.1-200 | 0° C.-120° C. | [d] | [e] | Group (1) | yes | 1:50-1:2,000 | [g] |
| 0.1-200 | 0° C.-120° C. | [d] | [e] | Group (1) | no | 1:50-1:2,000 | [g] |
| 0.1-200 | 10° C.-100° C. | [d] | [e] | Group (1) | yes | 1:50-1:2,000 | [g] |
| 0.1-200 | 10° C.-100° C. | [d] | [e] | Group (1) | no | 1:50-1:2,000 | [g] |
| 0.1-200 | 20° C.-50° C. | [d] | [e] | Group (1) | yes | 1:50-1:2,000 | [g] |
| 0.1-200 | 20° C.-50° C. | [d] | [e] | Group (1) | no | 1:50-1:2,000 | [g] |
| 0.1-100 | 0° C.-250° C. | [d] | [e] | Group (1) | yes | 1:50-1:2,000 | [g] |
| 0.1-100 | 0° C.-250° C. | [d] | [e] | Group (1) | no | 1:50-1:2,000 | [g] |
| 0.1-100 | 0° C.-120° C. | [d] | [e] | Group (1) | yes | 1:50-1:2,000 | [g] |
| 0.1-100 | 0° C.-120° C. | [d] | [e] | Group (1) | no | 1:50-1:2,000 | [g] |
| 0.1-100 | 10° C.-100° C. | [d] | [e] | Group (1) | yes | 1:50-1:2,000 | [g] |
| 0.1-100 | 10° C.-100° C. | [d] | [e] | Group (1) | no | 1:50-1:2,000 | [g] |
| 0.1-100 | 20° C.-50° C. | [d] | [e] | Group (1) | yes | 1:50-1:2,000 | [g] |
| 0.1-100 | 20° C.-50° C. | [d] | [e] | Group (1) | no | 1:50-1:2,000 | [g] |
| 0.1-60 | 0° C.-250° C. | [d] | [e] | Group (1) | yes | 1:50-1:2,000 | [g] |

TABLE 3-continued

Preferred reaction conditions during the hydrogenation.

| Pressure [bar] | Temperatur [° C.] | Hydrogenation catalyst | Alkylating agent, molar ratio carbonyl: alkylating agent 1:1-1:2 | Base | Solvent | Molar ratio catalyst: starting material | Starting material |
|---|---|---|---|---|---|---|---|
| 0.1-60 | 0° C.-250° C. | [d] | [e] | Group (1) | no | 1:50-1:2,000 | [g] |
| 0.1-60 | 0° C.-120° C. | [d] | [e] | Group (1) | yes | 1:50-1:2,000 | [g] |
| 0.1-60 | 0° C.-120° C. | [d] | [e] | Group (1) | no | 1:50-1:2,000 | [g] |
| 0.1-60 | 10° C.-100° C. | [d] | [e] | Group (1) | yes | 1:50-1:2,000 | [g] |
| 0.1-60 | 10° C.-100° C. | [d] | [e] | Group (1) | no | 1:50-1:2,000 | [g] |
| 0.1-60 | 20° C.-50° C. | [d] | [e] | Group (1) | yes | 1:50-1:2,000 | [g] |
| 0.1-60 | 20° C.-50° C. | [d] | [e] | Group (1) | no | 1:50-1:2,000 | [g] |
| 0.1-200 | 0° C.-250° C. | [d] | [e] | Group (2) | yes | 1:50-1:2,000 | [g] |
| 0.1-200 | 0° C.-250° C. | [d] | [e] | Group (2) | no | 1:50-1:2,000 | [g] |
| 0.1-200 | 0° C.-120° C. | [d] | [e] | Group (2) | yes | 1:50-1:2,000 | [g] |
| 0.1-200 | 0° C.-120° C. | [d] | [e] | Group (2) | no | 1:50-1:2,000 | [g] |
| 0.1-200 | 10° C.-100° C. | [d] | [e] | Group (2) | yes | 1:50-1:2,000 | [g] |
| 0.1-200 | 10° C.-100° C. | [d] | [e] | Group (2) | no | 1:50-1:2,000 | [g] |
| 0.1-200 | 20° C.-50° C. | [d] | [e] | Group (2) | yes | 1:50-1:2,000 | [g] |
| 0.1-200 | 20° C.-50° C. | [d] | [e] | Group (2) | no | 1:50-1:2,000 | [g] |
| 0.1-100 | 0° C.-250° C. | [d] | [e] | Group (2) | yes | 1:50-1:2,000 | [g] |
| 0.1-100 | 0° C.-250° C. | [d] | [e] | Group (2) | no | 1:50-1:2,000 | [g] |
| 0.1-100 | 0° C.-120° C. | [d] | [e] | Group (2) | yes | 1:50-1:2,000 | [g] |
| 0.1-100 | 0° C.-120° C. | [d] | [e] | Group (2) | no | 1:50-1:2,000 | [g] |
| 0.1-100 | 10° C.-100° C. | [d] | [e] | Group (2) | yes | 1:50-1:2,000 | [g] |
| 0.1-100 | 10° C.-100° C. | [d] | [e] | Group (2) | no | 1:50-1:2,000 | [g] |
| 0.1-100 | 20° C.-50° C. | [d] | [e] | Group (2) | yes | 1:50-1:2,000 | [g] |
| 0.1-100 | 20° C.-50° C. | [d] | [e] | Group (2) | no | 1:50-1:2,000 | [g] |
| 0.1-60 | 0° C.-250° C. | [d] | [e] | Group (2) | yes | 1:50-1:2,000 | [g] |
| 0.1-60 | 0° C.-250° C. | [d] | [e] | Group (2) | no | 1:50-1:2,000 | [g] |
| 0.1-60 | 0° C.-120° C. | [d] | [e] | Group (2) | yes | 1:50-1:2,000 | [g] |
| 0.1-60 | 0° C.-120° C. | [d] | [e] | Group (2) | no | 1:50-1:2,000 | [g] |
| 0.1-60 | 10° C.-100° C. | [d] | [e] | Group (2) | yes | 1:50-1:2,000 | [g] |
| 0.1-60 | 10° C.-100° C. | [d] | [e] | Group (2) | no | 1:50-1:2,000 | [g] |
| 0.1-60 | 20° C.-50° C. | [d] | [e] | Group (2) | yes | 1:50-1:2,000 | [g] |
| 0.1-60 | 20° C.-50° C. | [d] | [e] | Group (2) | no | 1:50-1:2,000 | [g] |
| 0.1-200 | 0° C.-250° C. | [d] | [f] | Group (1) | yes | 1:50-1:2,000 | [g] |
| 0.1-200 | 0° C.-250° C. | [d] | [f] | Group (1) | no | 1:50-1:2,000 | [g] |
| 0.1-200 | 0° C.-120° C. | [d] | [f] | Group (1) | yes | 1:50-1:2,000 | [g] |
| 0.1-200 | 0° C.-120° C. | [d] | [f] | Group (1) | no | 1:50-1:2,000 | [g] |
| 0.1-200 | 10° C.-100° C. | [d] | [f] | Group (1) | yes | 1:50-1:2,000 | [g] |
| 0.1-200 | 10° C.-100° C. | [d] | [f] | Group (1) | no | 1:50-1:2,000 | [g] |
| 0.1-200 | 20° C.-50° C. | [d] | [f] | Group (1) | yes | 1:50-1:2,000 | [g] |
| 0.1-200 | 20° C.-50° C. | [d] | [f] | Group (1) | no | 1:50-1:2,000 | [g] |
| 0.1-100 | 0° C.-250° C. | [d] | [f] | Group (1) | yes | 1:50-1:2,000 | [g] |
| 0.1-100 | 0° C.-250° C. | [d] | [f] | Group (1) | no | 1:50-1:2,000 | [g] |
| 0.1-100 | 0° C.-120° C. | [d] | [f] | Group (1) | yes | 1:50-1:2,000 | [g] |
| 0.1-100 | 0° C.-120° C. | [d] | [f] | Group (1) | no | 1:50-1:2,000 | [g] |
| 0.1-100 | 10° C.-100° C. | [d] | [f] | Group (1) | yes | 1:50-1:2,000 | [g] |
| 0.1-100 | 10° C.-100° C. | [d] | [f] | Group (1) | no | 1:50-1:2,000 | [g] |
| 0.1-100 | 20° C.-50° C. | [d] | [f] | Group (1) | yes | 1:50-1:2,000 | [g] |
| 0.1-100 | 20° C.-50° C. | [d] | [f] | Group (1) | no | 1:50-1:2,000 | [g] |
| 0.1-60 | 0° C.-250° C. | [d] | [f] | Group (1) | yes | 1:50-1:2,000 | [g] |
| 0.1-60 | 0° C.-250° C. | [d] | [f] | Group (1) | no | 1:50-1:2,000 | [g] |
| 0.1-60 | 0° C.-120° C. | [d] | [f] | Group (1) | yes | 1:50-1:2,000 | [g] |
| 0.1-60 | 0° C.-120° C. | [d] | [f] | Group (1) | no | 1:50-1:2,000 | [g] |
| 0.1-60 | 10° C.-100° C. | [d] | [f] | Group (1) | yes | 1:50-1:2,000 | [g] |
| 0.1-60 | 10° C.-100° C. | [d] | [f] | Group (1) | no | 1:50-1:2,000 | [g] |
| 0.1-60 | 20° C.-50° C. | [d] | [f] | Group (1) | yes | 1:50-1:2,000 | [g] |
| 0.1-60 | 20° C.-50° C. | [d] | [f] | Group (1) | no | 1:50-1:2,000 | [g] |
| 0.1-200 | 0° C.-250° C. | [d] | [f] | Group (2) | yes | 1:50-1:2,000 | [g] |
| 0.1-200 | 0° C.-250° C. | [d] | [f] | Group (2) | no | 1:50-1:2,000 | [g] |
| 0.1-200 | 0° C.-120° C. | [d] | [f] | Group (2) | yes | 1:50-1:2,000 | [g] |
| 0.1-200 | 0° C.-120° C. | [d] | [f] | Group (2) | no | 1:50-1:2,000 | [g] |
| 0.1-200 | 10° C.-100° C. | [d] | [f] | Group (2) | yes | 1:50-1:2,000 | [g] |
| 0.1-200 | 10° C.-100° C. | [d] | [f] | Group (2) | no | 1:50-1:2,000 | [g] |
| 0.1-200 | 20° C.-50° C. | [d] | [f] | Group (2) | yes | 1:50-1:2,000 | [g] |
| 0.1-200 | 20° C.-50° C. | [d] | [f] | Group (2) | no | 1:50-1:2,000 | [g] |
| 0.1-100 | 0° C.-250° C. | [d] | [f] | Group (2) | yes | 1:50-1:2,000 | [g] |
| 0.1-100 | 0° C.-250° C. | [d] | [f] | Group (2) | no | 1:50-1:2,000 | [g] |
| 0.1-100 | 0° C.-120° C. | [d] | [f] | Group (2) | yes | 1:50-1:2,000 | [g] |
| 0.1-100 | 0° C.-120° C. | [d] | [f] | Group (2) | no | 1:50-1:2,000 | [g] |
| 0.1-100 | 10° C.-100° C. | [d] | [f] | Group (2) | yes | 1:50-1:2,000 | [g] |
| 0.1-100 | 10° C.-100° C. | [d] | [f] | Group (2) | no | 1:50-1:2,000 | [g] |
| 0.1-100 | 20° C.-50° C. | [d] | [f] | Group (2) | yes | 1:50-1:2,000 | [g] |
| 0.1-100 | 20° C.-50° C. | [d] | [f] | Group (2) | no | 1:50-1:2,000 | [g] |
| 0.1-60 | 0° C.-250° C. | [d] | [f] | Group (2) | yes | 1:50-1:2,000 | [g] |

TABLE 3-continued

Preferred reaction conditions during the hydrogenation.

| Pressure [bar] | Temperatur [° C.] | Hydrogenation catalyst | Alkylating agent, molar ratio carbonyl: alkylating agent 1:1-1:2 | Base | Solvent | Molar ratio catalyst: starting material | Starting material |
|---|---|---|---|---|---|---|---|
| 0.1-60 | 0° C.-250° C. | [d] | [f] | Group (2) | no | 1:50-1:2,000 | [g] |
| 0.1-60 | 0° C.-120° C. | [d] | [f] | Group (2) | yes | 1:50-1:2,000 | [g] |
| 0.1-60 | 0° C.-120° C. | [d] | [f] | Group (2) | no | 1:50-1:2,000 | [g] |
| 0.1-60 | 10° C.-100° C. | [d] | [f] | Group (2) | yes | 1:50-1:2,000 | [g] |
| 0.1-60 | 10° C.-100° C. | [d] | [f] | Group (2) | no | 1:50-1:2,000 | [g] |
| 0.1-60 | 20° C.-50° C. | [d] | [f] | Group (2) | yes | 1:50-1:2,000 | [g] |
| 0.1-60 | 20° C.-50° C. | [d] | [f] | Group (2) | no | 1:50-1:2,000 | [g] |
| 0.1-200 | 0° C.-250° C. | [d] | [e] | Group (1) | yes | 1:50-1:2,000 | [h] |
| 0.1-200 | 0° C.-250° C. | [d] | [e] | Group (1) | no | 1:50-1:2,000 | [h] |
| 0.1-200 | 0° C.-120° C. | [d] | [e] | Group (1) | yes | 1:50-1:2,000 | [h] |
| 0.1-200 | 0° C.-120° C. | [d] | [e] | Group (1) | no | 1:50-1:2,000 | [h] |
| 0.1-200 | 10° C.-100° C. | [d] | [e] | Group (1) | yes | 1:50-1:2,000 | [h] |
| 0.1-200 | 10° C.-100° C. | [d] | [e] | Group (1) | no | 1:50-1:2,000 | [h] |
| 0.1-200 | 20° C.-50° C. | [d] | [e] | Group (1) | yes | 1:50-1:2,000 | [h] |
| 0.1-200 | 20° C.-50° C. | [d] | [e] | Group (1) | no | 1:50-1:2,000 | [h] |
| 0.1-100 | 0° C.-250° C. | [d] | [e] | Group (1) | yes | 1:50-1:2,000 | [h] |
| 0.1-100 | 0° C.-250° C. | [d] | [e] | Group (1) | no | 1:50-1:2,000 | [h] |
| 0.1-100 | 0° C.-120° C. | [d] | [e] | Group (1) | yes | 1:50-1:2,000 | [h] |
| 0.1-100 | 0° C.-120° C. | [d] | [e] | Group (1) | no | 1:50-1:2,000 | [h] |
| 0.1-100 | 10° C.-100° C. | [d] | [e] | Group (1) | yes | 1:50-1:2,000 | [h] |
| 0.1-100 | 10° C.-100° C. | [d] | [e] | Group (1) | no | 1:50-1:2,000 | [h] |
| 0.1-100 | 20° C.-50° C. | [d] | [e] | Group (1) | yes | 1:50-1:2,000 | [h] |
| 0.1-100 | 20° C.-50° C. | [d] | [e] | Group (1) | no | 1:50-1:2,000 | [h] |
| 0.1-60 | 0° C.-250° C. | [d] | [e] | Group (1) | yes | 1:50-1:2,000 | [h] |
| 0.1-60 | 0° C.-250° C. | [d] | [e] | Group (1) | no | 1:50-1:2,000 | [h] |
| 0.1-60 | 0° C.-120° C. | [d] | [e] | Group (1) | yes | 1:50-1:2,000 | [h] |
| 0.1-60 | 0° C.-120° C. | [d] | [e] | Group (1) | no | 1:50-1:2,000 | [h] |
| 0.1-60 | 10° C.-100° C. | [d] | [e] | Group (1) | yes | 1:50-1:2,000 | [h] |
| 0.1-60 | 10° C.-100° C. | [d] | [e] | Group (1) | no | 1:50-1:2,000 | [h] |
| 0.1-60 | 20° C.-50° C. | [d] | [e] | Group (1) | yes | 1:50-1:2,000 | [h] |
| 0.1-60 | 20° C.-50° C. | [d] | [e] | Group (1) | no | 1:50-1:2,000 | [h] |
| 0.1-200 | 0° C.-250° C. | [d] | [e] | Group (2) | yes | 1:50-1:2,000 | [h] |
| 0.1-200 | 0° C.-250° C. | [d] | [e] | Group (2) | no | 1:50-1:2,000 | [h] |
| 0.1-200 | 0° C.-120° C. | [d] | [e] | Group (2) | yes | 1:50-1:2,000 | [h] |
| 0.1-200 | 0° C.-120° C. | [d] | [e] | Group (2) | no | 1:50-1:2,000 | [h] |
| 0.1-200 | 10° C.-100° C. | [d] | [e] | Group (2) | yes | 1:50-1:2,000 | [h] |
| 0.1-200 | 10° C.-100° C. | [d] | [e] | Group (2) | no | 1:50-1:2,000 | [h] |
| 0.1-200 | 20° C.-50° C. | [d] | [e] | Group (2) | yes | 1:50-1:2,000 | [h] |
| 0.1-200 | 20° C.-50° C. | [d] | [e] | Group (2) | no | 1:50-1:2,000 | [h] |
| 0.1-100 | 0° C.-250° C. | [d] | [e] | Group (2) | yes | 1:50-1:2,000 | [h] |
| 0.1-100 | 0° C.-250° C. | [d] | [e] | Group (2) | no | 1:50-1:2,000 | [h] |
| 0.1-100 | 0° C.-120° C. | [d] | [e] | Group (2) | yes | 1:50-1:2,000 | [h] |
| 0.1-100 | 0° C.-120° C. | [d] | [e] | Group (2) | no | 1:50-1:2,000 | [h] |
| 0.1-100 | 10° C.-100° C. | [d] | [e] | Group (2) | yes | 1:50-1:2,000 | [h] |
| 0.1-100 | 10° C.-100° C. | [d] | [e] | Group (2) | no | 1:50-1:2,000 | [h] |
| 0.1-100 | 20° C.-50° C. | [d] | [e] | Group (2) | yes | 1:50-1:2,000 | [h] |
| 0.1-100 | 20° C.-50° C. | [d] | [e] | Group (2) | no | 1:50-1:2,000 | [h] |
| 0.1-60 | 0° C.-250° C. | [d] | [e] | Group (2) | yes | 1:50-1:2,000 | [h] |
| 0.1-60 | 0° C.-250° C. | [d] | [e] | Group (2) | no | 1:50-1:2,000 | [h] |
| 0.1-60 | 0° C.-120° C. | [d] | [e] | Group (2) | yes | 1:50-1:2,000 | [h] |
| 0.1-60 | 0° C.-120° C. | [d] | [e] | Group (2) | no | 1:50-1:2,000 | [h] |
| 0.1-60 | 10° C.-100° C. | [d] | [e] | Group (2) | yes | 1:50-1:2,000 | [h] |
| 0.1-60 | 10° C.-100° C. | [d] | [e] | Group (2) | no | 1:50-1:2,000 | [h] |
| 0.1-60 | 20° C.-50° C. | [d] | [e] | Group (2) | yes | 1:50-1:2,000 | [h] |
| 0.1-60 | 20° C.-50° C. | [d] | [e] | Group (2) | no | 1:50-1:2,000 | [h] |
| 0.1-200 | 0° C.-250° C. | [d] | [f] | Group (1) | yes | 1:50-1:2,000 | [h] |
| 0.1-200 | 0° C.-250° C. | [d] | [f] | Group (1) | no | 1:50-1:2,000 | [h] |
| 0.1-200 | 0° C.-120° C. | [d] | [f] | Group (1) | yes | 1:50-1:2,000 | [h] |
| 0.1-200 | 0° C.-120° C. | [d] | [f] | Group (1) | no | 1:50-1:2,000 | [h] |
| 0.1-200 | 10° C.-100° C. | [d] | [f] | Group (1) | yes | 1:50-1:2,000 | [h] |
| 0.1-200 | 10° C.-100° C. | [d] | [f] | Group (1) | no | 1:50-1:2,000 | [h] |
| 0.1-200 | 20° C.-50° C. | [d] | [f] | Group (1) | yes | 1:50-1:2,000 | [h] |
| 0.1-200 | 20° C.-50° C. | [d] | [f] | Group (1) | no | 1:50-1:2,000 | [h] |
| 0.1-100 | 0° C.-250° C. | [d] | [f] | Group (1) | yes | 1:50-1:2,000 | [h] |
| 0.1-100 | 0° C.-250° C. | [d] | [f] | Group (1) | no | 1:50-1:2,000 | [h] |
| 0.1-100 | 0° C.-120° C. | [d] | [f] | Group (1) | yes | 1:50-1:2,000 | [h] |
| 0.1-100 | 0° C.-120° C. | [d] | [f] | Group (1) | no | 1:50-1:2,000 | [h] |
| 0.1-100 | 10° C.-100° C. | [d] | [f] | Group (1) | yes | 1:50-1:2,000 | [h] |
| 0.1-100 | 10° C.-100° C. | [d] | [f] | Group (1) | no | 1:50-1:2,000 | [h] |
| 0.1-100 | 20° C.-50° C. | [d] | [f] | Group (1) | yes | 1:50-1:2,000 | [h] |
| 0.1-100 | 20° C.-50° C. | [d] | [f] | Group (1) | no | 1:50-1:2,000 | [h] |
| 0.1-60 | 0° C.-250° C. | [d] | [f] | Group (1) | yes | 1:50-1:2,000 | [h] |

TABLE 3-continued

Preferred reaction conditions during the hydrogenation.

| Pressure [bar] | Temperatur [° C.] | Hydrogenation catalyst | Alkylating agent, molar ratio carbonyl: alkylating agent 1:1-1:2 | Base | Solvent | Molar ratio catalyst: starting material | Starting material |
|---|---|---|---|---|---|---|---|
| 0.1-60 | 0° C.-250° C. | [d] | [f] | Group (1) | no | 1:50-1:2,000 | [h] |
| 0.1-60 | 0° C.-120° C. | [d] | [f] | Group (1) | yes | 1:50-1:2,000 | [h] |
| 0.1-60 | 0° C.-120° C. | [d] | [f] | Group (1) | no | 1:50-1:2,000 | [h] |
| 0.1-60 | 10° C.-100° C. | [d] | [f] | Group (1) | yes | 1:50-1:2,000 | [h] |
| 0.1-60 | 10° C.-100° C. | [d] | [f] | Group (1) | no | 1:50-1:2,000 | [h] |
| 0.1-60 | 20° C.-50° C. | [d] | [f] | Group (1) | yes | 1:50-1:2,000 | [h] |
| 0.1-60 | 20° C.-50° C. | [d] | [f] | Group (1) | no | 1:50-1:2,000 | [h] |
| 0.1-200 | 0° C.-250° C. | [d] | [f] | Group (2) | yes | 1:50-1:2,000 | [h] |
| 0.1-200 | 0° C.-250° C. | [d] | [f] | Group (2) | no | 1:50-1:2,000 | [h] |
| 0.1-200 | 0° C.-120° C. | [d] | [f] | Group (2) | yes | 1:50-1:2,000 | [h] |
| 0.1-200 | 0° C.-120° C. | [d] | [f] | Group (2) | no | 1:50-1:2,000 | [h] |
| 0.1-200 | 10° C.-100° C. | [d] | [f] | Group (2) | yes | 1:50-1:2,000 | [h] |
| 0.1-200 | 10° C.-100° C. | [d] | [f] | Group (2) | no | 1:50-1:2,000 | [h] |
| 0.1-200 | 20° C.-50° C. | [d] | [f] | Group (2) | yes | 1:50-1:2,000 | [h] |
| 0.1-200 | 20° C.-50° C. | [d] | [f] | Group (2) | no | 1:50-1:2,000 | [h] |
| 0.1-100 | 0° C.-250° C. | [d] | [f] | Group (2) | yes | 1:50-1:2,000 | [h] |
| 0.1-100 | 0° C.-250° C. | [d] | [f] | Group (2) | no | 1:50-1:2,000 | [h] |
| 0.1-100 | 0° C.-120° C. | [d] | [f] | Group (2) | yes | 1:50-1:2,000 | [h] |
| 0.1-100 | 0° C.-120° C. | [d] | [f] | Group (2) | no | 1:50-1:2,000 | [h] |
| 0.1-100 | 10° C.-100° C. | [d] | [f] | Group (2) | yes | 1:50-1:2,000 | [h] |
| 0.1-100 | 10° C.-100° C. | [d] | [f] | Group (2) | no | 1:50-1:2,000 | [h] |
| 0.1-100 | 20° C.-50° C. | [d] | [f] | Group (2) | yes | 1:50-1:2,000 | [h] |
| 0.1-100 | 20° C.-50° C. | [d] | [f] | Group (2) | no | 1:50-1:2,000 | [h] |
| 0.1-60 | 0° C.-250° C. | [d] | [f] | Group (2) | yes | 1:50-1:2,000 | [h] |
| 0.1-60 | 0° C.-250° C. | [d] | [f] | Group (2) | no | 1:50-1:2,000 | [h] |
| 0.1-60 | 0° C.-120° C. | [d] | [f] | Group (2) | yes | 1:50-1:2,000 | [h] |
| 0.1-60 | 0° C.-120° C. | [d] | [f] | Group (2) | no | 1:50-1:2,000 | [h] |
| 0.1-60 | 10° C.-100° C. | [d] | [f] | Group (2) | yes | 1:50-1:2,000 | [h] |
| 0.1-60 | 10° C.-100° C. | [d] | [f] | Group (2) | no | 1:50-1:2,000 | [h] |
| 0.1-60 | 20° C.-50° C. | [d] | [f] | Group (2) | yes | 1:50-1:2,000 | [h] |
| 0.1-60 | 20° C.-50° C. | [d] | [f] | Group (2) | no | 1:50-1:2,000 | [h] |
| 0.1-200 | 0° C.-250° C. | [d] | [e] | Group (1) | yes | 1:50-1:2,000 | [i] |
| 0.1-200 | 0° C.-250° C. | [d] | [e] | Group (1) | no | 1:50-1:2,000 | [i] |
| 0.1-200 | 0° C.-120° C. | [d] | [e] | Group (1) | yes | 1:50-1:2,000 | [i] |
| 0.1-200 | 0° C.-120° C. | [d] | [e] | Group (1) | no | 1:50-1:2,000 | [i] |
| 0.1-200 | 10° C.-100° C. | [d] | [e] | Group (1) | yes | 1:50-1:2,000 | [i] |
| 0.1-200 | 10° C.-100° C. | [d] | [e] | Group (1) | no | 1:50-1:2,000 | [i] |
| 0.1-200 | 20° C.-50° C. | [d] | [e] | Group (1) | yes | 1:50-1:2,000 | [i] |
| 0.1-200 | 20° C.-50° C. | [d] | [e] | Group (1) | no | 1:50-1:2,000 | [i] |
| 0.1-100 | 0° C.-250° C. | [d] | [e] | Group (1) | yes | 1:50-1:2,000 | [i] |
| 0.1-100 | 0° C.-250° C. | [d] | [e] | Group (1) | no | 1:50-1:2,000 | [i] |
| 0.1-100 | 0° C.-120° C. | [d] | [e] | Group (1) | yes | 1:50-1:2,000 | [i] |
| 0.1-100 | 0° C.-120° C. | [d] | [e] | Group (1) | no | 1:50-1:2,000 | [i] |
| 0.1-100 | 10° C.-100° C. | [d] | [e] | Group (1) | yes | 1:50-1:2,000 | [i] |
| 0.1-100 | 10° C.-100° C. | [d] | [e] | Group (1) | no | 1:50-1:2,000 | [i] |
| 0.1-100 | 20° C.-50° C. | [d] | [e] | Group (1) | yes | 1:50-1:2,000 | [i] |
| 0.1-100 | 20° C.-50° C. | [d] | [e] | Group (1) | no | 1:50-1:2,000 | [i] |
| 0.1-60 | 0° C.-250° C. | [d] | [e] | Group (1) | yes | 1:50-1:2,000 | [i] |
| 0.1-60 | 0° C.-250° C. | [d] | [e] | Group (1) | no | 1:50-1:2,000 | [i] |
| 0.1-60 | 0° C.-120° C. | [d] | [e] | Group (1) | yes | 1:50-1:2,000 | [i] |
| 0.1-60 | 0° C.-120° C. | [d] | [e] | Group (1) | no | 1:50-1:2,000 | [i] |
| 0.1-60 | 10° C.-100° C. | [d] | [e] | Group (1) | yes | 1:50-1:2,000 | [i] |
| 0.1-60 | 10° C.-100° C. | [d] | [e] | Group (1) | no | 1:50-1:2,000 | [i] |
| 0.1-60 | 20° C.-50° C. | [d] | [e] | Group (1) | yes | 1:50-1:2,000 | [i] |
| 0.1-60 | 20° C.-50° C. | [d] | [e] | Group (1) | no | 1:50-1:2,000 | [i] |
| 0.1-200 | 0° C.-250° C. | [d] | [e] | Group (2) | yes | 1:50-1:2,000 | [i] |
| 0.1-200 | 0° C.-250° C. | [d] | [e] | Group (2) | no | 1:50-1:2,000 | [i] |
| 0.1-200 | 0° C.-120° C. | [d] | [e] | Group (2) | yes | 1:50-1:2,000 | [i] |
| 0.1-200 | 0° C.-120° C. | [d] | [e] | Group (2) | no | 1:50-1:2,000 | [i] |
| 0.1-200 | 10° C.-100° C. | [d] | [e] | Group (2) | yes | 1:50-1:2,000 | [i] |
| 0.1-200 | 10° C.-100° C. | [d] | [e] | Group (2) | no | 1:50-1:2,000 | [i] |
| 0.1-200 | 20° C.-50° C. | [d] | [e] | Group (2) | yes | 1:50-1:2,000 | [i] |
| 0.1-200 | 20° C.-50° C. | [d] | [e] | Group (2) | no | 1:50-1:2,000 | [i] |
| 0.1-100 | 0° C.-250° C. | [d] | [e] | Group (2) | yes | 1:50-1:2,000 | [i] |
| 0.1-100 | 0° C.-250° C. | [d] | [e] | Group (2) | no | 1:50-1:2,000 | [i] |
| 0.1-100 | 0° C.-120° C. | [d] | [e] | Group (2) | yes | 1:50-1:2,000 | [i] |
| 0.1-100 | 0° C.-120° C. | [d] | [e] | Group (2) | no | 1:50-1:2,000 | [i] |
| 0.1-100 | 10° C.-100° C. | [d] | [e] | Group (2) | yes | 1:50-1:2,000 | [i] |
| 0.1-100 | 10° C.-100° C. | [d] | [e] | Group (2) | no | 1:50-1:2,000 | [i] |
| 0.1-100 | 20° C.-50° C. | [d] | [e] | Group (2) | yes | 1:50-1:2,000 | [i] |
| 0.1-100 | 20° C.-50° C. | [d] | [e] | Group (2) | no | 1:50-1:2,000 | [i] |
| 0.1-60 | 0° C.-250° C. | [d] | [e] | Group (2) | yes | 1:50-1:2,000 | [i] |

TABLE 3-continued

Preferred reaction conditions during the hydrogenation.

| Pressure [bar] | Temperatur [° C.] | Hydrogenation catalyst | Alkylating agent, molar ratio carbonyl: alkylating agent 1:1-1:2 | Base | Solvent | Molar ratio catalyst: starting material | Starting material |
|---|---|---|---|---|---|---|---|
| 0.1-60 | 0° C.-250° C. | [d] | [e] | Group (2) | no | 1:50-1:2,000 | [i] |
| 0.1-60 | 0° C.-120° C. | [d] | [e] | Group (2) | yes | 1:50-1:2,000 | [i] |
| 0.1-60 | 0° C.-120° C. | [d] | [e] | Group (2) | no | 1:50-1:2,000 | [i] |
| 0.1-60 | 10° C.-100° C. | [d] | [e] | Group (2) | yes | 1:50-1:2,000 | [i] |
| 0.1-60 | 10° C.-100° C. | [d] | [e] | Group (2) | no | 1:50-1:2,000 | [i] |
| 0.1-60 | 20° C.-50° C. | [d] | [e] | Group (2) | yes | 1:50-1:2,000 | [i] |
| 0.1-60 | 20° C.-50° C. | [d] | [e] | Group (2) | no | 1:50-1:2,000 | [i] |
| 0.1-200 | 0° C.-250° C. | [d] | [f] | Group (1) | yes | 1:50-1:2,000 | [i] |
| 0.1-200 | 0° C.-250° C. | [d] | [f] | Group (1) | no | 1:50-1:2,000 | [i] |
| 0.1-200 | 0° C.-120° C. | [d] | [f] | Group (1) | yes | 1:50-1:2,000 | [i] |
| 0.1-200 | 0° C.-120° C. | [d] | [f] | Group (1) | no | 1:50-1:2,000 | [i] |
| 0.1-200 | 10° C.-100° C. | [d] | [f] | Group (1) | yes | 1:50-1:2,000 | [i] |
| 0.1-200 | 10° C.-100° C. | [d] | [f] | Group (1) | no | 1:50-1:2,000 | [i] |
| 0.1-200 | 20° C.-50° C. | [d] | [f] | Group (1) | yes | 1:50-1:2,000 | [i] |
| 0.1-200 | 20° C.-50° C. | [d] | [f] | Group (1) | no | 1:50-1:2,000 | [i] |
| 0.1-100 | 0° C.-250° C. | [d] | [f] | Group (1) | yes | 1:50-1:2,000 | [i] |
| 0.1-100 | 0° C.-250° C. | [d] | [f] | Group (1) | no | 1:50-1:2,000 | [i] |
| 0.1-100 | 0° C.-120° C. | [d] | [f] | Group (1) | yes | 1:50-1:2,000 | [i] |
| 0.1-100 | 0° C.-120° C. | [d] | [f] | Group (1) | no | 1:50-1:2,000 | [i] |
| 0.1-100 | 10° C.-100° C. | [d] | [f] | Group (1) | yes | 1:50-1:2,000 | [i] |
| 0.1-100 | 10° C.-100° C. | [d] | [f] | Group (1) | no | 1:50-1:2,000 | [i] |
| 0.1-100 | 20° C.-50° C. | [d] | [f] | Group (1) | yes | 1:50-1:2,000 | [i] |
| 0.1-100 | 20° C.-50° C. | [d] | [f] | Group (1) | no | 1:50-1:2,000 | [i] |
| 0.1-60 | 0° C.-250° C. | [d] | [f] | Group (1) | yes | 1:50-1:2,000 | [i] |
| 0.1-60 | 0° C.-250° C. | [d] | [f] | Group (1) | no | 1:50-1:2,000 | [i] |
| 0.1-60 | 0° C.-120° C. | [d] | [f] | Group (1) | yes | 1:50-1:2,000 | [i] |
| 0.1-60 | 0° C.-120° C. | [d] | [f] | Group (1) | no | 1:50-1:2,000 | [i] |
| 0.1-60 | 10° C.-100° C. | [d] | [f] | Group (1) | yes | 1:50-1:2,000 | [i] |
| 0.1-60 | 10° C.-100° C. | [d] | [f] | Group (1) | no | 1:50-1:2,000 | [i] |
| 0.1-60 | 20° C.-50° C. | [d] | [f] | Group (1) | yes | 1:50-1:2,000 | [i] |
| 0.1-60 | 20° C.-50° C. | [d] | [f] | Group (1) | no | 1:50-1:2,000 | [i] |
| 0.1-200 | 0° C.-250° C. | [d] | [f] | Group (2) | yes | 1:50-1:2,000 | [i] |
| 0.1-200 | 0° C.-250° C. | [d] | [f] | Group (2) | no | 1:50-1:2,000 | [i] |
| 0.1-200 | 0° C.-120° C. | [d] | [f] | Group (2) | yes | 1:50-1:2,000 | [i] |
| 0.1-200 | 0° C.-120° C. | [d] | [f] | Group (2) | no | 1:50-1:2,000 | [i] |
| 0.1-200 | 10° C.-100° C. | [d] | [f] | Group (2) | yes | 1:50-1:2,000 | [i] |
| 0.1-200 | 10° C.-100° C. | [d] | [f] | Group (2) | no | 1:50-1:2,000 | [i] |
| 0.1-200 | 20° C.-50° C. | [d] | [f] | Group (2) | yes | 1:50-1:2,000 | [i] |
| 0.1-200 | 20° C.-50° C. | [d] | [f] | Group (2) | no | 1:50-1:2,000 | [i] |
| 0.1-100 | 0° C.-250° C. | [d] | [f] | Group (2) | yes | 1:50-1:2,000 | [i] |
| 0.1-100 | 0° C.-250° C. | [d] | [f] | Group (2) | no | 1:50-1:2,000 | [i] |
| 0.1-100 | 0° C.-120° C. | [d] | [f] | Group (2) | yes | 1:50-1:2,000 | [i] |
| 0.1-100 | 0° C.-120° C. | [d] | [f] | Group (2) | no | 1:50-1:2,000 | [i] |
| 0.1-100 | 10° C.-100° C. | [d] | [f] | Group (2) | yes | 1:50-1:2,000 | [i] |
| 0.1-100 | 10° C.-100° C. | [d] | [f] | Group (2) | no | 1:50-1:2,000 | [i] |
| 0.1-100 | 20° C.-50° C. | [d] | [f] | Group (2) | yes | 1:50-1:2,000 | [i] |
| 0.1-100 | 20° C.-50° C. | [d] | [f] | Group (2) | no | 1:50-1:2,000 | [i] |
| 0.1-60 | 0° C.-250° C. | [d] | [f] | Group (2) | yes | 1:50-1:2,000 | [i] |
| 0.1-60 | 0° C.-250° C. | [d] | [f] | Group (2) | no | 1:50-1:2,000 | [i] |
| 0.1-60 | 0° C.-120° C. | [d] | [f] | Group (2) | yes | 1:50-1:2,000 | [i] |
| 0.1-60 | 0° C.-120° C. | [d] | [f] | Group (2) | no | 1:50-1:2,000 | [i] |
| 0.1-60 | 10° C.-100° C. | [d] | [f] | Group (2) | yes | 1:50-1:2,000 | [i] |
| 0.1-60 | 10° C.-100° C. | [d] | [f] | Group (2) | no | 1:50-1:2,000 | [i] |
| 0.1-60 | 20° C.-50° C. | [d] | [f] | Group (2) | yes | 1:50-1:2,000 | [i] |
| 0.1-60 | 20° C.-50° C. | [d] | [f] | Group (2) | no | 1:50-1:2,000 | [i] |
| 40 bar $H_2$ | 20° C.-50° C. | [d] | [f] | $K_2CO_3$ [a], NaOEt | yes | 1:20-1:10,000 | [i] |
| 40 bar $H_2$ | 20°-50° C. | [d] | [f] | $K_2CO_3$ [a], NaOEt | no | 1:20-1:10,000 | [i] |
| 40 bar $H_2$ | 20° C.-50° C. | [d] | [f] | none | yes | 1:20-1:10,000 | [i] |
| 40 bar $H_2$ | 20°-50° C. | [d] | [f] | none | no | 1:20-1:10,000 | [i] |
| 40 bar $H_2$ | 20° C.-50° C. | [d] | [f] | $K_2CO_3$ [a], NaOEt | yes | 1:50-1:2,000 | [i] |
| 40 bar $H_2$ | 20°-50° C. | [d] | [f] | $K_2CO_3$ [a], NaOEt | no | 1:50-1:2,000 | [i] |

TABLE 3-continued

Preferred reaction conditions during the hydrogenation.

| Pressure [bar] | Temperatur [° C.] | Hydrogenation catalyst | Alkylating agent, molar ratio carbonyl: alkylating agent 1:1-1:2 | Base | Solvent | Molar ratio catalyst: starting material | Starting material |
|---|---|---|---|---|---|---|---|
| 40 bar $H_2$ | 20° C.-50° C. | [d] | [f] | none | yes | 1:50-1:2,000 | [i] |
| 40 bar $H_2$ | 20°-50° C. | [d] | [f] | none | no | 1:50-1:2,000 | [i] |

[a] = Addition of a phase transfer catalyst
[b] = Hydrogenation catalyst with at least one active metal of group VII B and/or VIII B of the Periodic Table of the Elements
[c] = Pd/C, Pd/Al$_2$O$_3$, Pd/CaCO$_3$, Pt/C, Ru/Al$_2$O$_3$, Pd/Re/C, Pt/Re/C or [(dppb)Rh(cod)]BF$_4$
[d] = 5% Pd/C, 5% Pd/Al$_2$O$_3$, 5% Pd/CaCO$_3$, 5% Pt/C, 5% Ru/Al$_2$O$_3$ or [(dppb)Rh(cod)]BF$_4$
[e] = Alkyl halides, esters of sulphonic acid, esters of fluorosulphonic acid, esters of trifluoromethanesulphonic acid, esters of chloroformic acid, oxonium salts, dialkyl sulphates or diazomethane,
[f] = (Me$_3$O)BF$_4$, (Et$_3$O)BF$_4$, (MeO)$_2$SO$_2$, (EtO)$_2$SO$_2$, ClCOOEt, MeI or EtI
[g] = Carboxylic acid amide of the general formula (I), carboxylic acid diamide of the general formula (II), di-, tri- or polypeptide, peptide amide with carboxy-terminal amide function,
[h] = Carboxylic acid amide of the general formula (I)
[i] = Carboxylic acid amides from Table 1

A particular embodiment of the invention is a process for the preparation of amines, where the alkylating agent is selected from the group consisting of alkyl halides, esters of sulphonic acid, esters of fluorosulphonic acid, esters of trifluoromethanesulphonic acid, esters of chloroformic acid, oxonium salts, dialkyl sulphates and diazomethane.

A further particular embodiment of the invention is a process for the preparation of amines, where the hydrogenation catalyst comprises at least one active metal.

A further particular embodiment of the invention is a process for the preparation of amines, where the active metal is a metal of group VII B and/or VIII B of the Periodic Table of the Elements.

A further particular embodiment of the invention is a process for the preparation of amines, where, after step a, a base is added to the reaction mixture and where a molar ratio of base to alkylating agent of from 1:1 to 1:3 is selected.

In principle, the person skilled in the art is free to choose a suitable basic compound. Preferably, however, cost-effective inorganic or organic bases are used.

The base can be selected from the group (1) consisting of carbonates, hydrogencarbonates, phosphates, mono- or dihydrogenphosphates or alkoxides of the alkali metals or alkaline earth metals;
nitrogen-containing organic molecules such as e.g. those selected from the group consisting of triethylamine, tri-n-butylamine, 1,4-diazabicyclo[2.2.2]octane, 1,8-diazabicyclo[5.4.0]undec-7-ene, N,N-dimethylglycine ethyl ester, pyridine, tetramethylguanidine, N,N,N',N'-tetramethylethane-1,2-diamine, hexamethylenetetramine; and amines supported on oligomers and polymers, and derivatives thereof.

Solid bases are preferably used in the presence of a phase transfer catalyst (PTC). Examples of phase transfer catalysts are the following compounds
dimethyl(di-(C$_{14}$-C$_{18}$)alkyl) ammonium chloride,
methyltri(C$_3$-C$_{10}$)alkylammonium chloride,
benzyldimethylstearylammonium chloride,
dimethyl-(C$_{12}$-C$_{16}$)-alkylbenzylammonium chloride,
distearyldimethylammonium chloride (Coconut oil alkyl)bis (2-hydroxyethyl,ethoxylated)methylammonium chloride (=PEG-2-cocomonium chloride),
hexadecyl(2-hydroxyethyl)dimethylammonium dihydrogenphosphate,
trihexyltetradecylphosphonium chloride,
trihexyltetradecylphosphonium bis(2,4,4-trimethylpentyl) phosphinate,
N,N-di(2-tallowamidoethyl)-N-(2-hydroxyethyl)-N-methylammonium methylsulphate,
di(oleyl-carboxyethyl)hydroxyethylmethylammonium methylsulphate,
di(palm-carboxyethyl)hydroxyethylmethylammonium methylsulphate,
bis(soybean-amidoethyl)polyethoxymethylammonium methylsulphate,
1-methyl-2-nortallow-3-tallow-amidoethyl-imidazolinium methylsulphate,
1-ethyl-3-heptadecenylimidazolinium methylsulphate,
1-methyl-2-noroleyl-3-oleylalkylamidoethylimidazolinium methylsulphate.

Preference is given to those bases which are selected from the group (2) consisting of K$_3$PO$_4$, K$_2$HPO$_4$, Ca$_2$CO$_3$, K$_2$CO$_3$, Na$_2$CO$_3$, NaOEt, NaOMe, NEt$_3$ and pyridine, where these bases are preferably used in the presence of a phase transfer catalyst.

The amount of base used can be freely selected by the person skilled in the art, with a molar ratio of base to alkylating agent of from 1:1 to 1:3 being preferred. Particular preference is given to a molar ratio of 1:1.

A particular embodiment of the invention is a process for the preparation of amines, where the reaction is carried out in a solvent.

A particular embodiment of the invention is a process for the preparation of amines, where the solvent is selected from the group consisting of hydrocarbons, chlorinated hydrocarbons, ethers, esters and alcohols.

A further particular embodiment of the invention is a process for the preparation of amines, where the reaction is carried out without solvents.

A further particular embodiment of the invention is a process for the preparation of amines, where the reaction is carried out without solvents.

It is advantageous to work in the absence of water. The invention therefore further provides a process where anhydrous carboxylic acid amide or carboxylic acid diamide or di-, tri- or polypeptide or peptide amide and anhydrous alkylating agent and optionally anhydrous solvent are used.

The invention further provides an amine obtainable by a process comprising the following steps:

a. reaction of a
  i. carboxylic acid amide of the general formula (I)

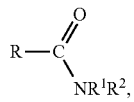

where
  R is selected from the group consisting of H, $(C_1-C_{24})$-alkyl, $(C_3-C_{20})$-cycloalkyl, $(C_2-C_{13})$-heterocycloalkyl, $(C_6-C_{14})$-aryl, $(C_3-C_{13})$-heteroaryl and the acid radical of an amino acid selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine; and
  $R^1$ and $R^2$, independently of one another, are selected from the group consisting of H, $(C_1-C_{24})$-alkyl, $(C_3-C_8)$-cycloalkyl, $(C_2-C_7)$-heterocycloalkyl, $(C_6-C_{14})$-aryl or $(C_3-C_{13})$-heteroaryl, where both the radicals R with $R^1$, R with $R^2$ and also $R^1$ with $R^2$, independently of one another, form a saturated or mono- or polyunsaturated $(C_2-C_{18})$-alkylene or $(C_2-C_{18})$-heteroalkylene bridge, such that an aliphatic or aromatic ring having in total 3-20 ring atoms is formed,
  or
  ii. carboxylic acid diamide of the general formula (II)

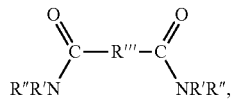

where
  R''' is selected from the group consisting of divalent $(C_1-C_{24})$-alkyl radicals, $(C_3-C_{20})$-cycloalkyl radicals, $(C_2-C_{13})$-heterocycloalkyl radicals, $(C_6-C_{14})$-aryl radicals, $(C_3-C_{13})$-heteroaryl radicals; and
  R' and R'', independently of one another, are selected from the group consisting of H, $(C_1-C_{24})$-alkyl, $(C_1-C_{24})$-heteroalkyl, $(C_3-C_8)$-cycloalkyl, $(C_2-C_7)$-heterocycloalkyl, $(C_6-C_{14})$-aryl or $(C_3-C_{13})$-heteroaryl, where the radicals R' with R'' can together form a saturated or mono- or polyunsaturated $(C_2-C_{18})$-alkylene or $(C_2-C_{18})$-heteroalkylene bridge, such that an aliphatic or aromatic ring having in total 3-20 ring atoms is formed,
  or
  iii. di-, tri- or polypeptide, or
  iv. peptide amide with carboxy-terminal amide function
with an alkylating agent,
b. addition of a hydrogenation catalyst to the reaction mixture in a molar ratio of from 1:10 to 1:100 000 based on carboxylic acid amide, carboxylic acid diamide di-, tri- or polypeptide or peptide amide,
c. reaction of the reaction mixture with hydrogen, where a hydrogen pressure of from 0.1 bar to 200 bar is established and where a temperature in a range of from 0° C. to 250° C. is established.

A particularly preferred embodiment is a process comprising the following steps:

a. reaction of a
  i. carboxylic acid amide of the general formula (I)

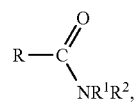

where
  R is selected from the group consisting of H, $(C_1-C_{24})$-alkyl, $(C_3-C_{20})$-cycloalkyl, $(C_2-C_{13})$-heterocycloalkyl, $(C_6-C_{14})$-aryl, $(C_3-C_{13})$-heteroaryl and the acid radical of an amino acid selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine; and
  $R^1$ and $R^2$, independently of one another, are selected from the group consisting of H, $(C_1-C_{24})$-alkyl, $(C_3-C_8)$-cycloalkyl, $(C_2-C_7)$-heterocycloalkyl, $(C_6-C_{14})$-aryl or $(C_3-C_{13})$-heteroaryl, where both the radicals R with $R^1$, R with $R^2$ and also $R^1$ with $R^2$, independently of one another, form a saturated or mono- or polyunsaturated $(C_2-C_{18})$-alkylene or $(C_2-C_{18})$-heteroalkylene bridge, such that an aliphatic or aromatic ring having in total 3-20 ring atoms is formed,
with an alkylating agent,
b. addition of a hydrogenation catalyst to the reaction mixture in a molar ratio of from 1:10 to 1:100 000, based on the carboxylic acid amide,
c. reaction of the reaction mixture with hydrogen, where a hydrogen pressure of from 0.1 bar to 200 bar is established and where a temperature in a range of from 0° C. to 250° C. is established.

In the process according to the invention, the procedure generally involves leaving the carboxylic acid amide or carboxylic acid diamide or di-, tri- or polypeptide or peptide amide and the alkylating agent to react together in an autoclave. The catalyst is then mixed in a certain molar ratio with a suitable amount of solvent. The autoclave is then flushed several times with hydrogen and the mixture is hydrogenated at a suitable pressure. After the hydrogen pressure has been let down, the reaction mixture is filtered off and the filtrate is worked up by processes known to the person skilled in the art.

In a preferred embodiment of the process according to the invention, the procedure generally involves leaving the carboxylic acid amide or carboxylic acid diamide or di-, tri- or polypeptide or peptide amide and the alkylating agent to react with one another in an autoclave. Mixing is then carried out with a suitable amount of solvent and base. The catalyst is then added in a certain molar ratio, the autoclave is flushed several times with hydrogen, and the mixture is hydrogenated at a suitable pressure. After the hydrogen pressure has been let down, the reaction mixture is filtered off and the filtrate is worked up by processes known to the person skilled in the art.

WORKING EXAMPLES

The examples below serve to illustrate the invention without limiting it thereto.

Examples 1-4

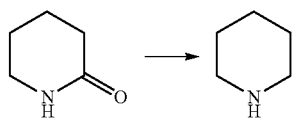

Example 1

Piperidone-2 (5 g, 50 mmol) is admixed with ethyl chloroformate (6 ml, 60 mmol) and stirred under argon for 4 hours at 50° C. Concentration in vacuo is then carried out, and the residue is taken up in absolute ethanol. An autoclave is charged with 5% Pt/C (0.98 g, 0.5 mol %), flushed with argon and filled with reaction solution in ethanol. 40 bar of hydrogen are then injected in, and the mixture is stirred at 25° C. and a constant pressure until hydrogen absorption is no longer evident (5 h). Following separation off from the catalyst, the filtrate is concentrated on a rotary evaporator, the residue is dissolved in 20 ml of water and washed with diethyl ether, the aqueous phase is rendered basic with 2N NaOH solution and etherified out. The organic phase is dried over $K_2CO_3$; after evaporating off the ether virtually clean piperidine is obtained.

The yield can be found in Table 4.

Example 2

Piperidone-2 (5 g, 50 mmol) is admixed with dimethyl sulphate (5 ml, 50 mmol) and stirred under argon for 3 hours at 80° C., and the product is then taken up in 10 ml of absolute methanol. An autoclave is charged with 5% Pt/C (0.98 g, 0.5 mol %), flushed with argon and filled with the reaction solution in methanol. 40 bar of hydrogen are then injected in, and the mixture is stirred at 25° C. and a constant pressure until hydrogen absorption is no longer evident (5 h). After separation off from the catalyst, the filtrate is concentrated on a rotary evaporator, the residue is dissolved in 20 ml of water and washed with diethyl ether, the aqueous phase is rendered basic with 2N NaOH solution and etherified out. The organic phase is dried over $K_2CO_3$; after evaporating off the ether virtually clean piperidine is obtained.

The yield can be found in Table 4.

Example 3

Piperidone-2 (5 g, 50 mmol) is admixed, with the exclusion of moisture and cooling on a water bath, with triethyloxonium tetrafluoroborate (10.45 g, 55 mmol). The water bath temperature is then gradually heated to 40° C., and stirring is carried out at this temperature for 1 hour. Then, the ether is drawn off in vacuo, and the residue is taken up in absolute ethanol. An autoclave is charged with 5% Pt/C (0.98 g, 0.5 mol %), flushed with argon and filled with the reaction mixture in ethanol. 40 bar of hydrogen are then injected in, and the mixture is stirred at 25° C. and a constant pressure until hydrogen absorption is no longer evident (5 h). After separation off from the catalyst, the filtrate is concentrated on a rotary evaporator, the residue is dissolved in 20 ml of water and washed with diethyl ether, the aqueous phase is rendered basic with 2N NaOH solution and etherified out. The organic phase is dried over $K_2CO_3$; after the ether has been evaporated off virtually clean piperidine is obtained.

The yield can be found in Table 4.

Example 4

Piperidone-2 (5 g, 50 mmol) is admixed, with the exclusion of moisture and cooling on a water bath, with triethyloxonium tetrafluoroborate (10.45 g, 55 mmol). Then, the water bath temperature is gradually heated to 40° C., and stirring is carried out at this temperature for 1 hour. Then, the ether is drawn off in vacuo, and the residue is taken up in absolute ethanol. An autoclave is charged with 5% Pt/C (0.98 g, 0.5 mol %) and $K_2CO_3$ (6.9 g, 50 mmol), flushed with argon and filled with the reaction mixture in ethanol. 40 bar of hydrogen are then injected in, and the mixture is stirred at 25° C. and a constant pressure until hydrogen absorption is no longer evident (5 h). After filtration over Celite, the filtrate is dissolved in 25 ml of 2N hydrochloric acid and washed with diethyl ether, the aqueous phase is rendered basic with 2N NaOH solution and etherified out, the organic phase is dried over $K_2CO_3$. After evaporating off the ether, virtually clean piperidine is obtained.

The yield can be found in Table 4.

TABLE 4

Reaction of piperidone-2 to piperidine.

| Example | Alkylating agent | Base | Yield, % |
|---|---|---|---|
| 1 | ClCOOEt | — | 80 |
| 2 | $(MeO)_2SO_2$ | — | 86 |
| 3 | $(Et_3O)BF_4$ | — | 85 |
| 4 | $(Et_3O)BF_4$ | $K_2CO_3$ | 86 |

Example 5

Pyrrolidone-2 (4.25 g, 50 mmol) is admixed with ethyl chloroformate (6 ml, 60 mmol) and stirred under argon for 4 hours at 50° C. Then, the mixture is concentrated in vacuo, and the residue is taken up in absolute ethanol. An autoclave is charged with 5% Pt/C (0.98 g, 0.5 mol %), flushed with argon and filled with the reaction solution in ethanol. 40 bar of hydrogen are then injected in, and the mixture is stirred at 25° C. and constant pressure for 24 hours. After separation off from the catalyst, the filtrate is concentrated on a rotary evaporator, the residue is dissolved in 20 ml of water and washed with diethyl ether, the aqueous phase is rendered basic with 2N NaOH solution and etherified out. The organic phase is dried over $K_2CO_3$; after the ether has been evaporated off virtually clean pyrrolidine is obtained. Yield 1.85 g (52%).

Examples 6-9

A carboxylic acid amide (10 mmol) is admixed with dimethyl sulphate (1 ml, 10 mmol) and stirred under argon for 3 hours at 80° C., and then the product is taken up in 5 ml of absolute methanol. An autoclave is charged with catalyst (1 mol %) and 5 ml of 2M sodium methylate solution in methanol, flushed with argon and filled with the reaction solution in methanol. 40 bar of hydrogen are then injected in, and the mixture is stirred at 25° C. and a constant pressure until hydrogen absorption is no longer evident (1-2 h). After filtration over Celite, the filtrate is dissolved in 10 ml of 2N hydrochloric acid and washed with diethyl ether, the aqueous phase is rendered basic with 12 ml of 2N NaOH solution and etherified out. The combined organic phases are dried over $K_2CO_3$ and admixed with 10 ml of 1M HCl solution in diethyl ether. The solid amine hydrochloride is filtered off, washed with diethyl ether and dried in vacuo.

The catalysts used and yields can be found in Table 5.

TABLE 5

| Example | Catalyst | Carboxylic acid amide | Product | Yield [%] |
|---|---|---|---|---|
| 6 | 5% Pd/C | cyclopentanone-NMe | pyrrolidine-NMe | 60 |
| 7 | 5% Ru/Al$_2$O$_3$ | cyclopentanone-NMe | pyrrolidine-NMe | 60 |
| 8 | 5% Pd/CaCO$_3$ | cycloheptanone-NMe | azepane-NMe | 50 |
| 9 | [(dppb)Rh(cod)]BF$_4$ | cycloheptanone-NMe | azepane-NMe | 60 |

Examples 10-28

A solution of carboxylic acid amide (20 mmol) in dichloromethane (10 ml) is admixed with triethyloxonium tetrafluoroborate (4.18 g, 22 mmol) and stirred either (A) overnight at room temperature or (B) for 3 hours on the water bath at 40° C. under argon. Then, the mixture is concentrated in vacuo and the residue is taken up in 20 ml of absolute ethanol. An autoclave cooled in the ice bath is charged with catalyst (1 mol %) and 10 ml of 2M sodiummethylate solution in ethanol, flushed with argon and filled with the reaction solution in ethanol. 40 bar of hydrogen are then injected in, and the mixture is stirred at 25° C. and a constant pressure until hydrogen absorption is no longer evident (1-12 h). After filtration over Celite, the filtrate is dissolved in 11 ml of 2N hydrochloric acid and washed with diethyl ether, the aqueous phase is rendered basic with 14 ml of 2N NaOH solution, the amine is extracted with diethyl ether, and the combined organic phases are dried over $K_2CO_3$. After drawing off the solvent in vacuo, virtually clean amine is obtained.

The catalysts used and yields can be found in Table 6.

TABLE 6

| Example | Catalyst | Starting material | Product | Yield, % |
|---|---|---|---|---|
| 10 [A] | 5% Pd/CaCO$_3$ | Ph-C(O)-NMe$_2$ | Ph-CH$_2$-NMe$_2$ | 69 |
| 11 [A] | 5% Pt/C | Ph-C(O)-NMe$_2$ | Ph-CH$_2$-NMe$_2$ | 68 |
| 12 [A] | [(dppb) Rh (cod)]BF$_4$ | Ph-C(O)-NMe$_2$ | Ph-CH$_2$-NMe$_2$ | 68 |
| 13 [A] | 5% Pd/Al$_2$O$_3$ | Ph-C(O)-NPr$^i_2$ | Ph-CH$_2$-NPr$^i_2$ | 62 |
| 14 [A] | 5% Pt/C | Ph-C(O)-NPr$^i_2$ | Ph-CH$_2$-NPr$^i_2$ | 72 |
| 15 [B] | 5% Pd/C | CH$_2$=CH-(CH$_2$)$_8$-C(O)-NMe$_2$ | CH$_2$=CH-(CH$_2$)$_8$-CH$_2$-NMe$_2$ | 78 |
| 16 [B] | 5% Pd/CaCO$_3$ | CH$_2$=CH-(CH$_2$)$_8$-C(O)-NMe$_2$ | CH$_2$=CH-(CH$_2$)$_8$-CH$_2$-NMe$_2$ | 78 |
| 17 [B] | 5% Pd/Al$_2$O$_3$ | CH$_2$=CH-(CH$_2$)$_8$-C(O)-NMe$_2$ | CH$_2$=CH-(CH$_2$)$_8$-CH$_2$-NMe$_2$ | 76 |

TABLE 6-continued

| Example | Catalyst | Starting material | Product | Yield, % |
|---|---|---|---|---|
| 18 [B] | [(dppb)Rh(cod)]BF₄ | CH₂=CH–(CH₂)₈–C(O)–NMe₂ | CH₂=CH–(CH₂)₈–NMe₂ | 71 |
| 19 [B] | 5% Pd/C | (EtO)₂P(O)–CH₂CH₂–C(O)–NMe₂ | (EtO)₂P(O)–CH₂CH₂CH₂–NMe₂ | 37 |
| 20 [B] | 5% Pt/C | (EtO)₂P(O)–CH₂CH₂–C(O)–NMe₂ | (EtO)₂P(O)–CH₂CH₂CH₂–NMe₂ | 35 |
| 21 [B] | 5% Ru/Al₂O₃ | (EtO)₂P(O)–CH₂CH₂–C(O)–NMe₂ | (EtO)₂P(O)–CH₂CH₂CH₂–NMe₂ | 39 |
| 22 [B] | [(dppb)Rh(cod)]BF₄ | (EtO)₂P(O)–CH₂CH₂–C(O)–NMe₂ | (EtO)₂P(O)–CH₂CH₂CH₂–NMe₂ | 39 |
| 23 [B] | 5% Pd/C | 2,3-dioxo-4-methylmorpholine | 3-oxo-4-methylmorpholine | 83 |
| 24 [B] | 5% Pd/CaCO₃ | 2,3-dioxo-4-methylmorpholine | 3-oxo-4-methylmorpholine | 98 |
| 25 [B] | 5% Pd/Al₂O₃ | 2,3-dioxo-4-methylmorpholine | 3-oxo-4-methylmorpholine | 98 |
| 26 [B] | [(dppb)Rh(cod)]BF₄ | 2,3-dioxo-4-methylmorpholine | 3-oxo-4-methylmorpholine | 93 |
| 27 [A] | 5% Pd/C | EtO–C(O)–C(O)–NHMe | EtO–C(O)–CH₂–NHMe | 34 |
| 28 [A] | 5% Pt/C | EtO–C(O)–C(O)–NHMe | EtO–C(O)–CH₂–NHMe | 37 |

Conditions: [A] stirred overnight at room temperature,
[B] stirred for 3 h at 40° C.

Examples 29-32

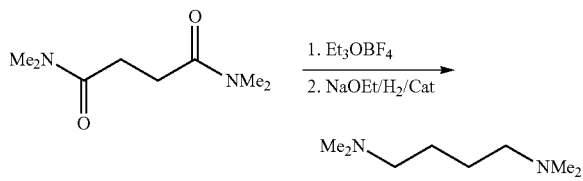

A solution of N,N'-tetramethylsuccinic acid diamide (20 mmol) in dichloromethane (20 ml) is admixed with triethyloxonium tetrafluoroborate (8.36 g, 44 mmol) and stirred under argon for 3 hours on the water bath at 40° C. The mixture is then concentrated in vacuo, and the residue is taken up in 50 ml of absolute ethanol. An autoclave cooled in the ice bath is charged with catalyst (1 mol %) and 20 ml of 2M sodiumethylate solution in ethanol, flushed with argon and filled with the reaction mixture in ethanol. 40 bar of hydrogen are then injected in, and the mixture is stirred at 25° C. and a constant pressure until hydrogen absorption is no longer evident (1-12 h). After filtration over Celite, the filtrate is worked up as in Examples 10-28.

The catalysts used and yields of N,N'-tetramethyl-1,4-butanediamine can be found in Table 7.

TABLE 7

Conversion of N,N'-tetramethylsuccinic acid diamide to N,N'-tetramethyl-1,4-butanediamine

| Example | Catalyst | Yield, % |
|---|---|---|
| 29 | 5% Pd/C | 60 |
| 30 | 5% Pd/Al$_2$O$_3$ | 62 |
| 31 | 5% Ru/Al$_2$O$_3$ | 63 |
| 32 | [(dppb)Rh(cod)]BF$_4$ | 67 |

Example 33

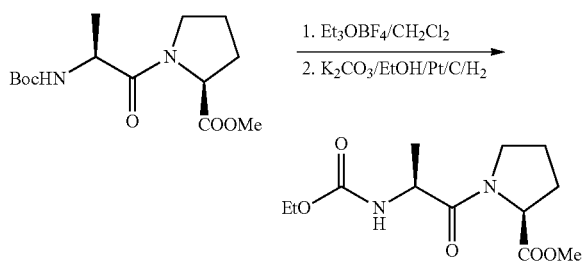

A solution of N-Boc-Ala-Pro-OMe (3.0 g, 10 mmol) in dichloromethane (10 ml) is admixed with triethyloxonium tetrafluoroborate (3.80 g, 20 mmol) and stirred under argon overnight at room temperature. Then, the mixture is concentrated in vacuo, and the residue is taken up in 20 ml of absolute ethanol. An autoclave is charged with 5% Pt/C (0.78 g, 2 mol %), trioctylmethylammonium chloride (Aliquat 336, 40 mg, 0.1 mmol) and K$_2$CO$_3$ (2.76 g, 20 mmol), flushed with argon and filled with the reaction mixture in ethanol. 40 bar of hydrogen are then injected in, and the mixture is stirred at 25° C. and constant pressure for 16 hours. After filtration over Celite, the filtrate is concentrated in vacuo, and the residue is purified by column chromatography (ethyl acetate/hexane 1:1). 1.42 g (55%) of (2'S,2S)-1-(2-ethoxycarbonylaminopropyl)pyrrolidine-2-carboxylic acid methyl ester (Rf 0.25) are obtained.

$^1$H NMR (CDCl$_3$) δ5.19 (br. s, 1H), 3.99-4.07 (m, 2H), 3.63 (s, 3H), 3.60 (q, J=6.4, 1H), 3.23 (dd, J=8.6, J=5.1, 1H), 3.09 (ddd, J=8.3, J=8.2, J=3.9, 1H), 2.60 (dd, J=12.4, J=6.0, 1H), 2.50 (dd, J=11.7, J=5.9, 1H), 2.47 (dt, J=8.9, J=7.5, 1H), 2.00-2.05 (m, 1H), 1.81-1.86 (m, 2H), 1.72-1.78 (m, 1H), 1.17 (t, J=7.1, 3H), 1.13 (d, J=6.6, 3H); $^{13}$C δ 174.80, 156.28, 66.50, 60.38, 60.20, 54.44, 51.69, 46.41, 29.39, 23.83, 19.48, 14.64.

Example 34

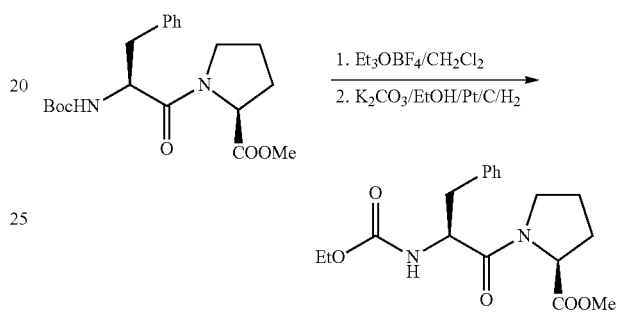

A solution of N-Boc-Phe-Pro-OMe (3.87 g, 10 mmol) in dichloromethane (10 ml) is admixed with triethyloxonium tetrafluoroborate (3.80 g, 20 mmol) and stirred under argon overnight at room temperature. Then, the mixture is concentrated in vacuo, and the residue is taken up in 20 ml of absolute ethanol. An autoclave is charged with 5% Pt/C (0.78 g, 2 mol %), trioctylmethylammonium chloride (Aliquat 336, 40 mg, 0.1 mmol) and K$_2$CO$_3$ (2.76 g, 20 mmol), flushed with argon and filled with the reaction mixture in ethanol. 40 bar of hydrogen are then injected in, and the mixture is stirred at 25° C. and constant pressure for 16 hours. After filtering over Celite, the filtrate is concentrated in vacuo, and the residue is purified by column chromatography (ethyl acetate/hexane 1:1). 1.18 g (34%) of (2'S,2S)-1-(2-ethoxycarbonylamino-3-phenylpropyl)pyrrolidine-2-carboxylic acid methyl ester (Rf 0.40) are obtained.

$^1$H NMR (CDCl$_3$) δ7.20 (t, J=7.6, 2H), 7.12 (t, J=7.8, 3H), 5.46 (br. s, 1H), 4.07 (dq, J=10.6, J=7.2, 1H), 4.02 (dq, J=10.6, J=7.1, 1H), 3.75 (br. m, 1H), 3.61 (s, 3H), 3.18 (br. m, 1H), 3.07 (br. m, 1H), 3.03 (td, J=7.9, J=3.4, 1H),2.58 (dd, J=13.5, J=7.8, 1H), 2.52 (t, J=11.3, 1H), 2.40 (dd, J=12.1, J=3.85, 1H), 2.21 (br. m, 1H), 1.98-2.04 (m, 1H), 1.98-2.04 (m, 1H), 1.66-1.72 (m, 2H), 1.18 (t, J=7.2, 3H); $^{13}$C δ 174.71, 156.84, 138.20, 129.48, 128.29, 126.25, 65.51, 60.54, 56.79, 53.04, 51.81, 51.44, 39.48, 29.21, 23.43, 14.69.

Example 35

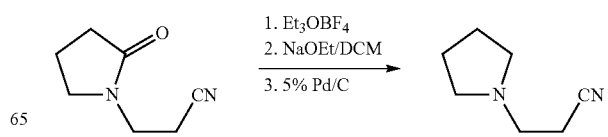

In a Schlenk vessel cooled in the ice bath, N-(2-cyanoethyl)pyrrolidone-2 (6.9 g, 50 mmol) is admixed with triethyloxonium tetrafluoroborate (10.45 g, 55 mmol) and stirred overnight at room temperature under argon. The ether phase is decanted off and any ether still present is removed in vacuo. The residue is dissolved in dry dichloromethane (40 ml) and added dropwise to a suspension of sodium ethoxide (ethanol-free) in 10 ml of dry diethyl ether at −20° C. Then, the mixture is left overnight to warm to room temperature with vigorous stirring and filtered off from the $NaBF_4$ under argon. The filtrate is concentrated and dissolved in 10 ml of dry dichloromethane. An autoclave is charged with 5% Pt/C (390 mg, 0.2 mol %), flushed with argon and filled with the reaction solution in dichloromethane. 40 bar of hydrogen are then injected in, and the mixture is stirred at 25° C. and constant pressure for 24 hours. After filtering over Celite, the filtrate is dissolved in 40 ml of ice-cold 2N hydrochloric acid and washed with diethyl ether, the aqueous phase is rendered basic under ice cooling with 42 ml of 2N NaOH solution, the product is extracted with diethyl ether (6×20 ml), and the combined organic phases are dried over $K_2CO_3$. After stripping off the solvent in vacuo, 2.6 g (44%) of virtually clean 3-(1-pyrrolidino)propionitrile are obtained.

The invention claimed is:

1. A process for the preparation of amines, comprising the steps:
    a) performing an O-alkylation of one or more compounds by reacting said compounds with an alkylating agent in a reaction mixture, wherein said alkylating agent is selected from the group consisting of: alkyl halides; esters of sulphonic acid; esters of fluorosulphonic acid; esters of trifluoromethanesulphonic acid; esters of chloroformic acid; oxonium salts; dialkyl sulphates; and diazomethane and said compounds are selected from the group consisting of:
        i) a carboxylic acid amide of the general formula (I):

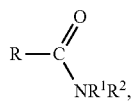

wherein:
            R is selected from the group consisting of: H, $(C_1-C_{24})$-alkyl, $(C_3-C_{20})$-cycloalkyl, $(C_2-C_{13})$-heterocycloalkyl, $(C_6-C_{14})$-aryl, $(C_3-C_{13})$-heteroaryl and the acid radical of an amino acid selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine; and
            $R^1$ and $R^2$, independently of one another, are selected from the group consisting of: H, $(C_1-C_{24})$-alkyl, $(C_3-C_8)$-cycloalkyl, $(C_2-C_7)$-heterocycloalkyl, $(C_6-C_{14})$-aryl or $(C_3-C_{13})$-heteroaryl, where both the radicals R with $R^1$, R with $R^2$ and also $R^1$ with $R^2$ may, independently of one another, form a saturated or mono- or polyunsaturated $(C_2-C_{18})$-alkylene or $(C_2-C_{18})$-heteroalkylene bridge, such that an aliphatic or aromatic ring having in total 3-20 ring atoms is formed;
        ii) a carboxylic acid diamide of the general formula (II):

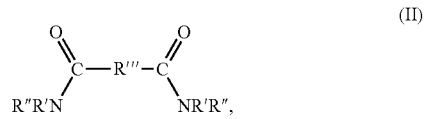

wherein:
            R''' is selected from the group consisting of divalent $(C_1-C_{24})$-alkyl radicals, $(C_3-C_{20})$-cycloalkyl radicals, $(C_2-C_{13})$-heterocycloalkyl radicals, $(C_6-C_{14})$-aryl radicals, $(C_3-C_{13})$-heteroaryl radicals; and
            R' and R'', independently of one another, are selected from the group consisting of H, $(C_1-C_{24})$-alkyl, $(C_1-C_{24})$-heteroalkyl, $(C_3-C_8)$-cycloalkyl, $(C_2-C_7)$-heterocycloalkyl, $(C_6-C_{14})$-aryl or $(C_3-C_{13})$-heteroaryl, where the radicals R' with R'' may together form a saturated or mono- or polyunsaturated $(C_2-C_{18})$-alkylene or $(C_2-C_{18})$-heteroalkylene bridge, such that an aliphatic or aromatic ring having in total 3-20 ring atoms is formed;
        iii) a di-, tri- or polypeptide, and
        iv) a peptide amide with a carboxy-terminal amide function;
    b) adding a hydrogenation catalyst to the reaction mixture, wherein the molar ratio of hydrogenation catalyst to carboxylic acid amide, or carboxylic acid diamide, or di-, tri- or polypeptide or peptide amide, is in a range of from 1:10 to 1:100 000;
    c) reacting the reaction mixture with hydrogen, at a hydrogen pressure of from 0.1 bar to 200 bar and at a temperature of from 0° C. to 250° C.

2. The process of claim 1, wherein the hydrogenation catalyst comprises at least one active metal.

3. The process of claim 2, wherein the active metal is a metal of group VII B and/or VIII B of the Periodic Table of the Elements.

4. The process of claim 1, wherein, after step a), a base is added to the reaction mixture and wherein a molar ratio of base to alkylating agent of from 1:1 to 1:3 is produced.

5. The process of claim 1, wherein the reaction is carried out in a solvent.

6. The process of claim 5, wherein the solvent is selected from the group consisting of: hydrocarbons; chlorinated hydrocarbons; ethers; esters; and alcohols.

7. The process of claim 1, wherein the reaction is carried out without solvents.

8. The process of claim 5, wherein said alkylating agent is anhydrous and wherein an anhydrous solvent is used.

9. The process of claim 1, wherein said compounds are carboxylic acid amides of the general formula (I):

wherein:
R is selected from the group consisting of: H, $(C_1-C_{24})$-alkyl, $(C_3-C_{20})$-cycloalkyl, $(C_2-C_{13})$-heterocycloalkyl, $(C_6-C_{14})$-aryl, $(C_3-C_{13})$-heteroaryl and the acid radical of an amino acid selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine; and $R^1$ and $R^2$, independently of one another, are selected from the group consisting of: H, $(C_1-C_{24})$-alkyl, $(C_3-C_8)$-cycloalkyl, $(C_2-C_7)$-heterocycloalkyl, $(C_6-C_{14})$-aryl or $(C_3-C_{13})$-heteroaryl, where both the radicals R with $R^1$, R with $R^2$ and also $R^1$ with $R^2$ may, independently of one another, form a saturated or mono- or polyunsaturated $(C_2-C_{18})$-alkylene or $(C_2-C_{18})$-heteroalkylene bridge, such that an aliphatic or aromatic ring having in total 3-20 ring atoms is formed.

10. The process of claim 9, wherein: R is H or a $C_1-C_6$ alkyl; and $R^1$ and $R^2$ are independently: H, a $(C_1-C_6)$-alkyl, $(C_3-C_8)$-cycloalkyl, $(C_2-C_7)$-heterocycloalkyl, a $(C_6-C_{14})$-aryl or a $(C_3-C_{13})$-heteroaryl.

11. The process of claim 1, wherein said compounds are carboxylic acid diamides of the general formula (II):

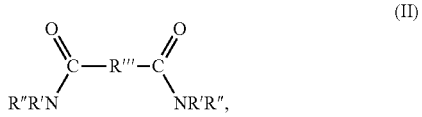

wherein:

R''' is selected from the group consisting of divalent $(C_1-C_{24})$-alkyl radicals, $(C_3-C_{20})$-cycloalkyl radicals, $(C_2-C_{13})$-heterocycloalkyl radicals, $(C_6-C_{14})$-aryl radicals, $(C_3-C_{13})$-heteroaryl radicals; and R' and R'', independently of one another, are selected from the group consisting of H, $(C_1-C_{24})$-alkyl, $(C_1-C_{24})$-heteroalkyl, $(C_3-C_8)$-cycloalkyl, $(C_2-C_7)$-heterocycloalkyl, $(C_6-C_{14})$-aryl or $(C_3-C_{13})$-heteroaryl, where the radicals R' with R'' may together form a saturated or mono- or polyunsaturated $(C_2-C_{18})$-alkylene or $(C_2-C_{18})$-heteroalkylene bridge, such that an aliphatic or aromatic ring having in total 3-20 ring atoms is formed.

12. The process of claim 1, wherein said compounds are one or more of the following: N,N,N',N'-tetramethylsuccinic acid diamide; N,N,N',N'-tetramethyladipic acid diamide; N,N,N',N'-tetramethylsuberic acid diamide, N,N,N',N'-tetramethylterephthalic acid diamide and sarcosine anhydride.

13. The process of claim 1, wherein said compounds are di-, tri- or polypeptides.

14. The process of claim 1, wherein said compounds are peptide amides with a carboxy-terminal amide function.

15. The process of claim 1, wherein said alkylating agent is an alkyl halide.

16. The process of claim 1, wherein said alkylating agent is an ester of sulphonic acid; an ester of fluorosulphonic acid; or and ester of trifluoromethanesulphonic acid.

17. The process of claim 1, wherein said alkylating agent is an ester of chloroformic acid.

18. The process of claim 1, wherein said alkylating agent is an oxonium salts.

19. The process of claim 1, wherein said alkylating agent is a dialkyl sulphate.

20. The process of claim 1, wherein said alkylating agent is diazomethane.

* * * * *